United States Patent
Tremblay et al.

(10) Patent No.: US 11,597,739 B2
(45) Date of Patent: Mar. 7, 2023

(54) ENHANCING CD8+ T CELLS FOR ADOPTIVE T CELL THERAPY BY INHIBITING PTPN1 (PTP1B) AND PTPN2 (TC-PTP)

(71) Applicant: The Royal Institution for the Advancement of Learning/McGill University, Montreal (CA)

(72) Inventors: Michel L. Tremblay, Montreal (CA); Kelly-Anne Pike, Dollard-des-Ormeaux (CA); Luis Alberto Perez Quintero, L'île-Bizard (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 325 days.

(21) Appl. No.: 16/641,533

(22) PCT Filed: Aug. 24, 2018

(86) PCT No.: PCT/CA2018/051025
§ 371 (c)(1),
(2) Date: Feb. 24, 2020

(87) PCT Pub. No.: WO2019/036815
PCT Pub. Date: Feb. 28, 2019

(65) Prior Publication Data
US 2021/0155645 A1    May 27, 2021

Related U.S. Application Data

(60) Provisional application No. 62/549,735, filed on Aug. 24, 2017.

(51) Int. Cl.
*C07F 9/6553* (2006.01)
*C12N 5/0783* (2010.01)

(52) U.S. Cl.
CPC ...... *C07F 9/655354* (2013.01); *C12N 5/0636* (2013.01)

(58) Field of Classification Search
CPC .................. C07F 9/655354; C12N 5/0636
USPC ......................................................... 514/80
See application file for complete search history.

(56) References Cited

FOREIGN PATENT DOCUMENTS

| WO | 2015127548 | 9/2015 |
| WO | 2015188228 | 12/2015 |

OTHER PUBLICATIONS

Cancer [online], [retrieved on Jul. 6, 2007] Retrieved from the Internet, URL: http://www.nim.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Berger, C et al. Adoptive transfer of effector CD8+ T cells derived from central memory cells establishes persistent T cell memory in primates. J Clin Invest. Jan. 2008 (Jan. 2008), vol. 118, pp. 294-305, ISSN: 0021-9738.

* cited by examiner

*Primary Examiner* — Kristin A Vajda
(74) *Attorney, Agent, or Firm* — Benoit & Cote Inc.

(57) ABSTRACT

The invention encompasses ex vivo method of stimulating isolated memory T-cell, tumor-infiltrating lymphocyte (TIL), T cell receptor (TCR) engineered cell, and/or chimeric antigen receptor (CAR) engineered cell with compounds of Formula I below, which are inhibitors of the TC-PTP enzyme.

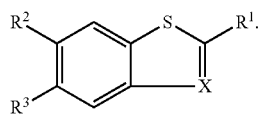

12 Claims, 13 Drawing Sheets

ENHANCING CD8+ T CELLS FOR ADOPTIVE T CELL THERAPY BY INHIBITING PTPN1 (PTP1B) AND PTPN2 (TC-PTP)

CROSS-REFERENCE TO RELATED APPLICATIONS

This application is a US National Phase application under 35 USC § 371 of PCT/CA2018/051025, filed Aug. 24, 2018, which claims priority from and the benefit of U.S. Provisional Patent Application No. 62/549,735, filed Aug. 24, 2017, the specifications of which are hereby incorporated by reference in their entireties.

FIELD OF THE INVENTION

This invention relates to the use of concomitant PTPN1 (PTP1B) and PTPN2 (TC-PTP) inhibitors to activate various types of T cells for application in immunotherapy treatment of disease.

BACKGROUND

T lymphocytes are a critical component of the immune system with the capacity to kill tumour cells. However, in cancer patients anti-tumour T cells are often in a non-functional state which limits their ability to eliminate tumours. Adoptive T cell therapy (ATCT) is an emerging strategy which involves isolating a cancer patient's own anti-tumour T cells and genetically modifying them to make them functional. This approach has increased the efficacy of cancer-based vaccines as the ex-vivo amplification of this T-cell population, and its transfer into cancer patients, effectively induces tumour regression. Nevertheless, ATCT still requires lymphodepletion and the administration of high dose interleukin-2 (IL-2), due to the immunosuppressive properties of the tumour microenvironment. Additionally, clinical trials have been hampered by the lack of reliable and reproducible persistence and activity of transferred T cells. While the administration of IL-2 has proven to enhance T cell persistence and function, the toxicity of systemic administration of IL-2, as well as the activation of T regulatory cells, presents limitations. Therefore, alternative approaches which amplify cytokine receptor signaling in transferred T cells would be of therapeutic benefit.

Dysregulation of the cytokine-activated Janus kinase-signal transducer and activator of transcription (JAK-STAT) pathway has been identified as one of the key factors responsible for the reduced T cell fitness and persistence. There are four members in the JAK family of tyrosine kinases: JAK1, JAK2, JAK3, and Tyk2 [Simoncic P D, et al. Curr Biol. 200212(6):446-453]. JAK kinases are constitutively associated with cytokine receptors and are activated by the binding of a cytokine to its cell-surface receptor. Once activated, the JAK kinase phosphorylates specific tyrosine residues on the receptor providing binding sites for STATs. STATs, consisting of 7 members: STAT1, STAT2, STAT3, STAT4, STAT5a, STAT5b, and STAT6, are a group of latent cytoplasmic transcription factors, which reside in an inactive form in the cytoplasm. They are activated by binding to the phosphorylation sites on cytokine receptors and are subsequently phosphorylated on a specific tyrosine residue by JAK. When phosphorylated they disassociate from the receptor, dimerize through their respective SH2 domains and enter the nucleus to induce expression of target genes. In addition to cytokine and chemokine receptors, JAK-STAT signaling can also be initiated directly by receptor tyrosine kinases such as Epidermal growth factor receptor, platelet derived growth factor receptor and others.

Protein tyrosine phosphatases (PTPs) are a family of transmembrane or intracellular enzymes that control multiple cellular regulatory processes by dephosphorylating phospho-tyrosine substrates. There are 107 PTPs in the human genome and several reviews have described in detail the members of this gene family. PTP1B (PTPN1) and TC-PTP (PTPN2) are two highly homologous classical non-receptor protein tyrosine phosphatases. TC-PTP (PTPN2) is found principally as a ~45 kD intracellular protein that localizes primarily to the nucleus and belongs to the class I subfamily of phosphotyrosine-specific PTPs. Although TC-PTP is ubiquitously expressed, highest expression is observed in all hematopoietic cells [Doody K M, et al. Immunol Rev. 2009 228: p 325-41; Tiganis, T., et al., J Biol Chem, 1999. 274(39): p. 27768-75; Arimura, Y. and J. Yagi, Sci Signal, 2010. 3(137): p. rs1.]. The C-terminal hydrophobic domain anchors PTP1B to the cytoplasmic face of the endoplasmic reticulum (ER) where is has been shown to target a wide range of substrates including tyrosine kinases, adaptors, cytoskeleton protein and transcription factors, and it has been implicated in diverse pathways including those controlling glucose uptake, proliferation, differentiation, cell mobility and adhesion [Pike, K A and Tremblay, M L, 82, 2016, p. 52-57].

The role of TC-PTP has been studied in several immune cell types. Inhibitors of TC-PTP have been used in the preparation of hematopoietic stem cells (HSC) and recently in dendritic cells (DCs). In these cases, using a knockout of TC-PTP or inhibitors thereof, the cell behavior appeared specific and associated with the particular JAK-STAT involved: IL-7 for the HSC and IL-4 for the DCs. TC-PTP inhibitors modified the transcriptomes in a dose-dependent manner. Furthermore, some redundancy in the control of immune responses is believed to exist between TC-PTP and PTP1B, which limits the effects of specific inhibition of either of both phosphatases. The inventors found that concomitant inhibition of TC-PTP and PTP1B, by genetic or pharmacological means, in CD8 T cells induced their spontaneous differentiation to T central memory cells (Tcm) a phenomenon previously unknown to the work described herein.

Hence, the inventors have found it surprising and unexpected that TC-PTP/PTP1B inhibitors could also provide a growth advantage and other phenotypes associated to the specific signaling induced by IL-15 in memory T cells as well as CD8 T cells over CD4 T cells. Therefore, this unique phenotype and the linked signaling cascades of IL-15 in a subset of T cells (CD8 vs CD4 vs memory and central memory T cell) were not predictable prior to the work described herein.

A number of methods are known for preparing tumor-infiltrating lymphocytes (TILs) for injection into patients [Dudley M E, et al. J Clin Oncol 26: 5233-5239, 2008; Besser M J, et al. Clin Cancer Res 19: 4792-4800, 2013; Rosenberg S A, et al. Clin Cancer Res 17: 4550-4557, 2011; Besser M J, et al. J Clin Oncol 23:2346-2357, 2005; Dudley M E, et al. J Immunother 26:332-342, 2003.]. Each of these published methods could be enhanced by the additional of a suitable inhibitor of TC-PTP as described herein.

A number of methods are known for preparing T-cell receptors (TCRs) engineered cells for injection into patients [Clay T M, et al. J Immunol. 1999; 163:507-513; Morgan R A, et al. J Immunol. 2003; 171:3287-3295; Schaft N, et al. J Immunol. 2003; 170:2186-2194; Zhao Y, et al. J Immunol.

2005; 174:4415-4423; Johnson L A, et al. Blood. 2009; 114:535-546; Morgan R A, et al. Science. 2006; 314:126-129]. Each of these published methods could be enhanced by the additional of a suitable inhibitor of TC-PTP as described herein.

A number of methods are known for preparing chimeric antigen receptor (CAR)-T cells for injection into patients [Porter D L, et al. N Engl J Med 2011; 365:725-33; Milone M C, et al. Mol Ther. 2009 August; 17(8):1453-64; Zhao Y, et al. Cancer Res. 2010 Nov. 15; 70(22):9053-61; Kalos M, et al. Sci Transl Med. 2011 Aug. 10; 3(95):95ra73; Hwu P I, et al. Cancer Res. 1995 Aug. 1; 55(15):3369-73; Wang G, et al. Nat Med. 1998 February; 4(2):168-72; Kochenderfer J N, et al. Blood. 2010 Nov. 18; 116(20):4099-102; Lee D W, et al. Lancet. 2015 Feb. 7; 385(9967):517-28; Kochenderfer J N, et al. J Clin Oncol. 2015 Feb. 20; 33(6):540-9]. Each of these published methods could be enhanced by the additional of a suitable inhibitor of TC-PTP as described herein.

SUMMARY

According to an embodiment, there is provided an ex vivo method of stimulating an isolated memory T-cell, tumor-infiltrating lymphocyte (TIL), T cell receptor (TCR) engineered cell, and/or chimeric antigen receptor (CAR) engineered cell comprising:

treating an isolated memory T-cell, tumor-infiltrating lymphocyte (TIL), T cell receptor (TCR) engineered cell, and/or chimeric antigen receptor (CAR) engineered cell with an effective amount of a compound of structural Formula I, or a pharmaceutically acceptable salts thereof, and stereoisomers thereof:

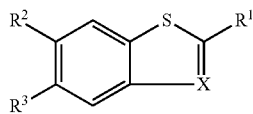

wherein:
X is selected from CH and N;
$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (b) —(C=O)$R^4$; (c) —CN; (d) —(C=O)$OR^4$; (e) —(C=O)NH$R^4$; (f) —(C=O)N$R^5R^6$; and (g) aryl or heteroaryl wherein the aryl and heteroaryl group itself may be optionally substituted with 1-3 substituents independently selected from (i) halogen, (ii) —(C=O)$OC_{1-3}$ alkyl optionally substituted with 1-3 halogens, (iii) —COOH (iv) $C_{1-3}$ alkyl optionally substituted with 1-3 halogens, (v) —$OC_{1-3}$ alkyl optionally substituted with 1-3 halogens, (vi) —$SO_x$Me, (vii) —CN, and (viii) —$SO_2NH_2$;
$R^2$ and $R^3$ are independently selected from the group consisting of (a) halogen; (b) difluoromethylphosphonic acid;
$R^4$ is selected from the group consisting of (a) H; (b) $C_{1-3}$alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (d) aryl or heteroaryl wherein the aryl or heteroaryl group itself may be optionally substituted by 1-3 halogens, $C_{1-3}$ alkyl or $C_{1-3}$ haloalkyl;
$R^5$ and $R^6$ are independently selected from the group consisting of (a) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (b) aryl or heteroaryl wherein the aryl or heteroaryl group itself may be optionally substituted by 1-3 halogens, $C_{1-3}$ alkyl or $C_{1-3}$ haloalkyl;
$R^5$ and $R^6$, together with the nitrogen atom to which they are attached may be joined to form a 5- to 7-membered ring, which may be substituted with 1-3 groups independently selected from (i) halogen, (ii) —(C=O)$OC_{1-3}$ alkyl, (iii) —(C=O)OH (iv) $C_{1-3}$ alkyl optionally substituted with 1-3 halogens, (v) —$OC_{1-3}$ alkyl optionally substituted with 1-3 halogens, (vi) —OH, (vii) $C_{1-3}$ hydroxyalkyl, (viii) aryl or heteroaryl wherein the aryl or heteroaryl group itself may be optionally substituted by 1-3 halogens, $C_{1-3}$ alkyl or $C_{1-3}$ haloalkyl; and
x is an integer from 0 to 2.

The compound may be of structural Formula Ia, or a pharmaceutically acceptable salts thereof, and stereoisomers thereof:

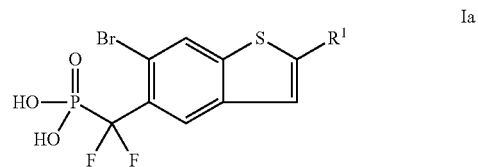

wherein:
$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, and —CN; (b) —(C=O)$R^4$; (c) —CN; (d) —(C=O)$OR^4$; (e) —(C=O)NH$R^4$; and (f) —(C=O)N$R^5R^6$;
$R^4$ is selected from the group consisting of (a) H; and (b) $C_{1-3}$ alkyl optionally substituted with 1-5 halogens;
$R^5$ and $R^6$ are independently selected from the group consisting of $C_{1-3}$ alkyl optionally substituted with 1-5 halogens and optionally with one group selected from —OH, and —$OC_{1-3}$ alkyl optionally substituted with 1-3 halogens; and
$R^5$ and $R^6$, together with the nitrogen atom to which they are attached may be joined to form a 5- to 7-membered ring, which may be substituted with a 1-3 groups independently selected from (i) halogen, (ii) $C_{1-3}$ alkyl optionally substituted with 1-3 halogens, (iii) —$OC_{1-3}$ alkyl optionally substituted with 1-3 halogens, (iv) —OH, and (vii) $C_{1-3}$ hydroxyalkyl.

The compound may be of structural Formula Ib, or a pharmaceutically acceptable salts thereof, and stereoisomers thereof:

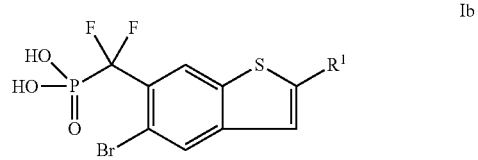

wherein:
$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, and —CN; (b) —(C═O)R⁴; (c) —CN; (d) —(C═O)OR⁴; (e) —(C═O)NHR⁴; and (f) —(C═O)NR⁵R⁶;

R⁴ is selected from the group consisting of (a) H; and (b) $C_{1-3}$ alkyl optionally substituted with 1-5 halogens;

R⁵ and R⁶ are independently selected from the group consisting of $C_{1-3}$ alkyl optionally substituted with 1-5 halogens and optionally with one group selected from —OH, and —$OC_{1-3}$ alkyl optionally substituted with 1-3 halogens; and R⁵ and R⁶, together with the nitrogen atom to which they are attached may be joined to form a 5- to 7-membered ring, which may be substituted with a 1-3 groups independently selected from (i) halogen, (ii) $C_{1-3}$ alkyl optionally substituted with 1-3 halogens, (iii) —$OC_{1-3}$ alkyl optionally substituted with 1-3 halogens, (iv) —OH, and (vii) $C_{1-3}$ hydroxyalkyl.

The compound may be a compound selected from the following compounds:

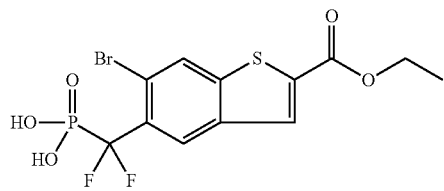

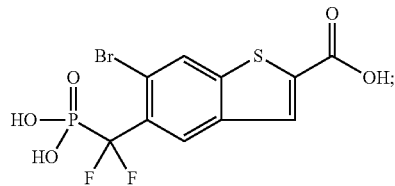

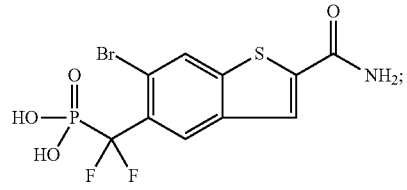

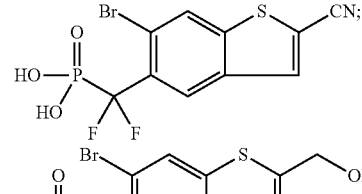

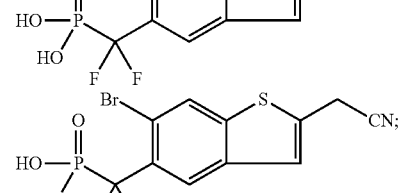

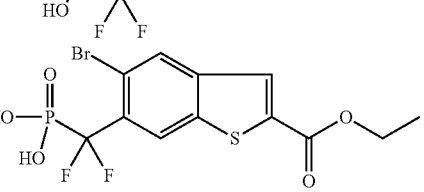

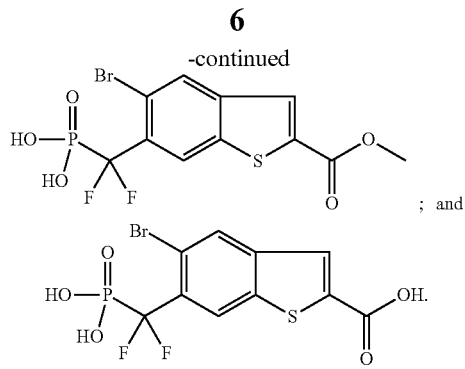

The compound may be selected from the following compounds:

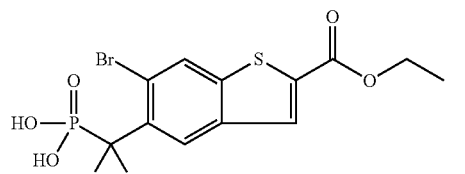

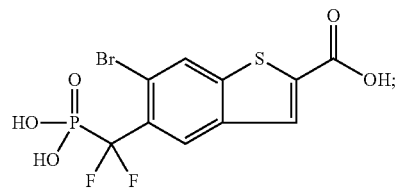

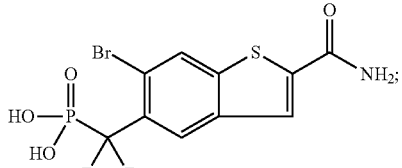

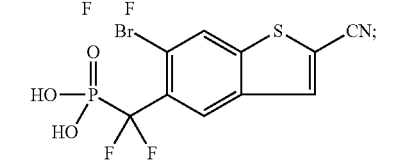

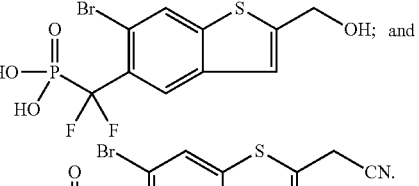

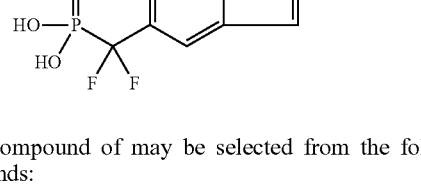

The compound of may be selected from the following compounds:

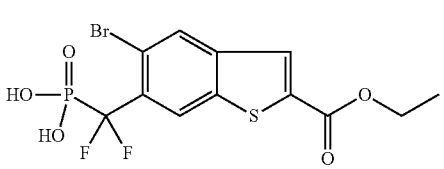

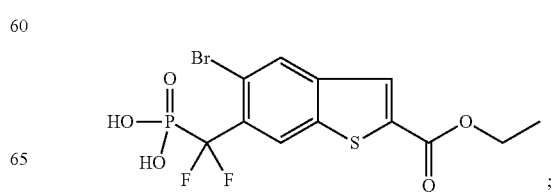

-continued

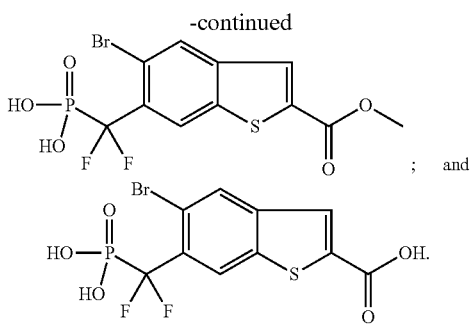
; and

7. The ex vivo method claim 2, wherein said compound may be

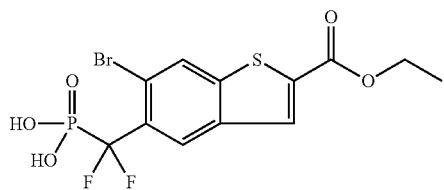

In the ex vivo method of the present invention, treating is under activating conditions.

The ex vivo method may further comprise the step of activating said isolated memory T-cell, tumor-infiltrating lymphocyte (TIL), T cell receptor (TCR) engineered cell, and/or chimeric antigen receptor (CAR) engineered cell before, during or after treatment with said compound of formula I, Ia or Ib.

The activating conditions or said step of activating comprises treatment with a cytokine, a chemokine, a growth factor, a T-cell associated check-point inhibitor, a tumor associated check-point inhibitor, antibodies recognizing CD3 and CD28 receptors, cytokines as IL-2, IL-7 and IL-15, autologous or allogeneic dendritic cells loaded with the specific antigen, any other antigen presenting cell (APC) loaded with the specific antigen, irradiated tumor cells treated or not with proinflammatory cytokines as type 1 and type 2 interferons, and combinations thereof.

In the ex vivo method of the present invention, treating may be for a time sufficient for expansion, transduction or activation of said isolated memory T-cell, tumor-infiltrating lymphocyte (TIL), T cell receptor (TCR) engineered cell, and/or chimeric antigen receptor (CAR) engineered cell.

The isolated tumor-infiltrating lymphocyte may be harvested from a patient.

The ex vivo method may further comprise the step of isolating memory T-cell, tumor-infiltrating lymphocyte (TIL), activated T cell receptor (TCR) engineered cell, and/or activated chimeric antigen receptor (CAR) engineered cell.

According to another embodiment, there may be provided a method of preventing or treating a disease in a patient in need thereof comprising:

administering an isolated memory T-cell, tumor-infiltrating lymphocyte (TIL), T cell receptor (TCR) engineered cell, and/or chimeric antigen receptor (CAR) engineered cell obtained by the method of any one of claims 8 to 13 to said patient.

The patient may be a patient unable to mount a sufficient immune response.

The disease may be a cancer, an immunosuppressive disease, an infectious disease, and combinations thereof.

The isolated tumor-infiltrating lymphocyte may be from the same patient.

The T-cell, tumor-infiltrating lymphocyte (TIL), T cell receptor (TCR) engineered cell, and/or chimeric antigen receptor (CAR) engineered cell may be injected into the bloodstream, into a lymph node, directly into a tumor, or directly into another tissue that has been impacted by the disease the patient may be being treated for.

The cancer may be selected from the group consisting of prostate cancer, breast cancer, brain cancer, glioma, lung cancer, salivary cancer, stomach cancer, thymic epithelial cancer, thyroid cancer, ovarian cancer, multiple myeloma, leukemia, melanoma, lymphoma, gastric cancer, kidney cancer, pancreatic cancer, bladder cancer, colon cancer and liver cancer.

The viral infection may be selected from the group consisting of an infection caused by cytomegalovirus Epstein-Barr virus, hepatitis B, hepatitis C virus, herpes virus, human immunodeficiency virus, human T lymphotropic virus, lymphocytic choriomeningitis virus, respiratory syncytial virus, and rhinovirus.

The bacterial infection may be selected from the group consisting of an infection caused by *Corynebacterium, Enterococcus, Escherichia, Haemophilius, Helicobacter, Legionella, Leptospira, Listeria, Mycobacterium, Neisseria, Porphyromonas, Pseudomonas, Salmonella, Staphylococcus* and *Chlamydia*.

The parasitic infection may be selected from the group consisting of infections caused by *Schistosoma, Leishmania, Plasmodium, Giardia, Trypanosoma* and *Taenia*.

The fungi infection may be selected from the group consisting of infections caused by *Aspergillus, Blastomyces, Candida*, Ringworm, and Murcormyces.

The T-cell, tumor-infiltrating lymphocyte (TIL), T cell receptor (TCR) engineered cell, and/or chimeric antigen receptor (CAR) engineered cell may be administered in sequence with, or in addition to one or more additional compounds selected from the group consisting of:
 (a) a cytotoxic agent;
 (b) an antimetabolite;
 (c) an alkylating agent;
 (d) an anthracycline;
 (e) an antibiotic;
 (f) an anti-mitotic agent;
 (g) an hormone therapy;
 (h) a signal transduction inhibitor;
 (i) a gene expression modulator;
 (j) an apoptosis inducer;
 (k) an angiogenesis inhibitor
 (l) an immunotherapy agent.

The cytotoxic agent may be selected from the group consisting of taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, analogs or homologs thereof, and combinations thereof.

The antimetabolites may be selected from the group consisting of methotrexate, 6-mercaptopurine, 6-thioguanine, gemcitabine, cytarabine, 5-fluorouracil decarbazine, and combinations thereof.

The alkylating agent may be selected from the group consisting of mechlorethamine, thioepa chlorambucil, melphalan, carmustine (BSNU), lomustine (CCNU), cyclothosphamide, busulfan, dibromomannitol, streptozotocin, mitomycin C, cis-dichlorodiamine platinum (II) (DDP) cisplatin, and combinations thereof.

The anthracycline may be selected from the group consisting of daunorubicin, doxorubicin, and combinations thereof.

The antibiotic may be selected from the group consisting of dactinomycin, bleomycin, mithramycin, anthramycin (AMC), and combinations thereof.

The anti-mitotic agent may be selected from the group consisting of vincristine, vinblastine, and combinations thereof.

The signal transduction inhibitor may be selected from the group consisting of imatinib, trastuzumab, PARPi, CDKi, and combinations thereof.

The gene expression modulator may be selected from the group consisting of a siRNA, a shRNA, an antisense oligonucleotide, an HDAC inhibitor, and combinations thereof.

The immunotherapy agent may be selected from the group consisting of a monoclonal antibody, a dendritic cell (DC) vaccine, an antigen therapy, and combinations thereof.

The hormone therapy may be a luteinizing hormone-releasing hormone (LHRH) antagonist.

The apoptosis inducers may be a recombinant human TNF-related apoptosis-inducing ligand (TRAIL).

The angiogenesis inhibitors may be selected from the group consisting of sorafenib, sunitinib, pazopanib, everolimus and combinations thereof.

The monoclonal antibody may be selected from the group consisting of anti-CTLA4, anti-PD1, anti-PD-1, anti-LAG3, anti-KIR, and combinations thereof.

According to another embodiment, there may be provided an isolated memory T-cell, tumor-infiltrating lymphocyte (TIL), T cell receptor (TCR) engineered cell, and/or chimeric antigen receptor (CAR) engineered cell obtained by the method of the present invention for use in preventing or treating a disease in a patient in need thereof.

The patient may be a patient unable to mount a sufficient immune response.

The disease may be a cancer, an immunosuppressive disease, an infectious disease, and combinations thereof.

The use of an isolated memory T-cell, tumor-infiltrating lymphocyte (TIL), T cell receptor (TCR) engineered cell, and/or chimeric antigen receptor (CAR) engineered cell obtained by the method of the present invention may be for preventing or treating a disease in a patient in need thereof.

The patient may be a patient unable to mount a sufficient immune response.

The disease may be a cancer, an immunosuppressive disease, an infectious disease, and combinations thereof.

The T-cell, tumor-infiltrating lymphocyte (TIL), T cell receptor (TCR) engineered cell, and/or chimeric antigen receptor (CAR) engineered cell may be for injection into the bloodstream, into a lymph node, directly into a tumor, or directly into another tissue that has been impacted by the disease the patient may be being treated for.

The cancer may be selected from the group consisting of prostate cancer, breast cancer, brain cancer, glioma, lung cancer, salivary cancer, stomach cancer, thymic epithelial cancer, thyroid cancer, ovarian cancer, multiple myeloma, leukemia, melanoma, lymphoma, gastric cancer, kidney cancer, pancreatic cancer, bladder cancer, colon cancer and liver cancer.

The viral infection may be selected from the group consisting of an infection caused by cytomegalovirus Epstein-Barr virus, hepatitis B, hepatitis C virus, herpes virus, human immunodeficiency virus, human T lymphotropic virus, lymphocytic choriomeningitis virus, respiratory syncytial virus, and rhinovirus.

The bacterial infection may be selected from the group consisting of an infection caused by *Corynebacterium, Enterococcus, Escherichia, Haemophilius, Helicobacter, Legionella, Leptospira, Listeria, Mycobacterium, Neisseria, Porphyromonas, Pseudomonas, Salmonella, Staphylococcus* and *Chlamydia*.

The parasitic infection may be selected from the group consisting of infections caused by *Schistosoma, Leishmania, Plasmodium, Giardia, Trypanosoma* and *Taenia*.

The fungi infection may be selected from the group consisting of infections caused by *Aspergillus, Blastomyces, Candida*, Ringworm, and Murcormyces.

The T-cell, tumor-infiltrating lymphocyte (TIL), T cell receptor (TCR) engineered cell, and/or chimeric antigen receptor (CAR) engineered cell may be administered in sequence with, or in addition to one or more additional compounds selected from the group consisting of:
 (a) a cytotoxic agent;
 (b) an antimetabolite;
 (c) an alkylating agent;
 (d) an anthracycline;
 (e) an antibiotic;
 (f) an anti-mitotic agent;
 (g) an hormone therapy;
 (h) a signal transduction inhibitor;
 (i) a gene expression modulator;
 (j) an apoptosis inducer;
 (k) an angiogenesis inhibitor
 (l) an immunotherapy agent.

The cytotoxic agent may be selected from the group consisting of taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, analogs or homologs thereof, and combinations thereof.

The antimetabolites may be selected from the group consisting of methotrexate, 6-mercaptopurine, 6-thioguanine, gemcitabine, cytarabine, 5-fluorouracil decarbazine, and combinations thereof.

The alkylating agent may be selected from the group consisting of mechlorethamine, thioepa chlorambucil, melphalan, carmustine (BSNU), lomustine (CCNU), cyclothosphamide, busulfan, dibromomannitol, streptozotocin, mitomycin C, cis-dichlorodiamine platinum (II) (DDP) cisplatin, and combinations thereof.

The anthracycline may be selected from the group consisting of daunorubicin, doxorubicin, and combinations thereof.

The antibiotic may be selected from the group consisting of dactinomycin, bleomycin, mithramycin, anthramycin (AMC), and combinations thereof.

The anti-mitotic agent may be selected from the group consisting of vincristine, vinblastine, and combinations thereof.

The signal transduction inhibitor may be selected from the group consisting of imatinib, trastuzumab, PARPi, CDKi and combinations thereof.

The gene expression modulator may be selected from the group consisting of a siRNA, a shRNA, an antisense oligonucleotide, an HDAC inhibitor, and combinations thereof.

The immunotherapy agent may be selected from the group consisting of a monoclonal antibody, a dendritic cell (DC) vaccine, an antigen therapy, and combinations thereof.

The hormone therapy may be a luteinizing hormone-releasing hormone (LHRH) antagonist.

The apoptosis inducers may be a recombinant human TNF-related apoptosis-inducing ligand (TRAIL).

The angiogenesis inhibitors may be selected from the group consisting of sorafenib, sunitinib, pazopanib, everolimus and combinations thereof.

The monoclonal antibody may be selected from the group consisting of anti-CTLA4, anti-PD1, anti-PD-1, anti-LAG3, anti-KIR, and combinations thereof.

According to another embodiment, there may be provided an in vitro method of stimulating a primary cell to produce activated cells suitable for therapeutic treatment of a patient in need of immunotherapy comprising:

treating an isolated primary cell with an effective amount of a compound of structural Formula I, or a pharmaceutically acceptable salts thereof, and stereoisomers thereof:

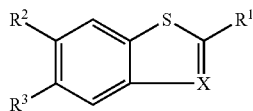

wherein:

X is selected from CH and N;

$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (b) —(C=O)$R^4$; (c) —CN; (d) —(C=O)$OR^4$; (e) —(C=O)$NHR^4$; (f) —(C=O)$NR^5R^6$; and (g) aryl or heteroaryl wherein the aryl and heteroaryl group itself may be optionally substituted with 1-3 substituents independently selected from (i) halogen, (ii) —(C=O)$OC_{1-3}$ alkyl optionally substituted with 1-3 halogens, (iii) —COOH (iv) $C_{1-3}$ alkyl optionally substituted with 1-3 halogens, (v) —$OC_{1-3}$ alkyl optionally substituted with 1-3 halogens, (vi) —$SO_x$Me, (vii) —CN, and (viii) —$SO_2NH_2$;

$R^2$ and $R^3$ are independently selected from the group consisting of (a) halogen; (b) difluoromethylphosphonic acid;

$R^4$ is selected from the group consisting of (a) H; (b) $C_{1-3}$alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (d) aryl or heteroaryl wherein the aryl or heteroaryl group itself may be optionally substituted by 1-3 halogens, $C_{1-3}$ alkyl or $C_{1-3}$ haloalkyl;

$R^5$ and $R^6$ are independently selected from the group consisting of (a) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (b) aryl or heteroaryl wherein the aryl or heteroaryl group itself may be optionally substituted by 1-3 halogens, $C_{1-3}$ alkyl or $C_{1-3}$ haloalkyl;

$R^5$ and $R^6$, together with the nitrogen atom to which they are attached may be joined to form a 5- to 7-membered ring, which may be substituted with 1-3 groups independently selected from (i) halogen, (ii) —(C=O)$OC_{1-3}$ alkyl, (iii) —(C=O)OH (iv) $C_{1-3}$ alkyl optionally substituted with 1-3 halogens, (v) —$OC_{1-3}$ alkyl optionally substituted with 1-3 halogens, (vi) —OH, (vii) $C_{1-3}$ hydroxyalkyl, (viii) aryl or heteroaryl wherein the aryl or heteroaryl group itself may be optionally substituted by 1-3 halogens, $C_{1-3}$ alkyl or $C_{1-3}$ haloalkyl; and x is an integer from 0 to 2.

The compound may be of structural Formula Ia, or a pharmaceutically acceptable salts thereof, and stereoisomers thereof:

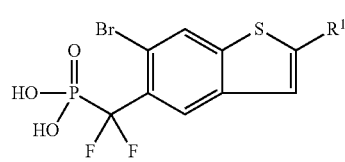

wherein:

$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, and —CN; (b) —(C=O)$R^4$; (c) —CN; (d) —(C=O)$OR^4$; (e) —(C=O)$NHR^4$; and (f) —(C=O)$NR^5R^6$;

$R^4$ is selected from the group consisting of (a) H; and (b) $C_{1-3}$ alkyl optionally substituted with 1-5 halogens;

$R^5$ and $R^6$ are independently selected from the group consisting of $C_{1-3}$ alkyl optionally substituted with 1-5 halogens and optionally with one group selected from —OH, and —$OC_{1-3}$ alkyl optionally substituted with 1-3 halogens; and $R^5$ and $R^6$, together with the nitrogen atom to which they are attached may be joined to form a 5- to 7-membered ring, which may be substituted with a 1-3 groups independently selected from (i) halogen, (ii) $C_{1-3}$ alkyl optionally substituted with 1-3 halogens, (iii) —$OC_{1-3}$ alkyl optionally substituted with 1-3 halogens, (iv) —OH, and (vii) $C_{1-3}$ hydroxyalkyl.

The compound may be of structural Formula Ib, or a pharmaceutically acceptable salts thereof, and stereoisomers thereof:

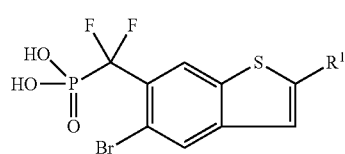

wherein:

$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, and —CN; (b) —(C=O)$R^4$; (c) —CN; (d) —(C=O)$OR^4$; (e) —(C=O)$NHR^4$; and (f) —(C=O)$NR^5R^6$;

$R^4$ is selected from the group consisting of (a) H; and (b) $C_{1-3}$ alkyl optionally substituted with 1-5 halogens;

$R^5$ and $R^6$ are independently selected from the group consisting of $C_{1-3}$ alkyl optionally substituted with 1-5 halogens and optionally with one group selected from —OH, and —$OC_{1-3}$ alkyl optionally substituted with 1-3 halogens; and $R^5$ and $R^6$, together with the nitrogen atom to which they are attached may be joined to form a 5- to 7-membered ring, which may be substituted with a 1-3 groups independently selected from (i) halogen, (ii) $C_{1-3}$ alkyl optionally substituted with 1-3 halogens, (iii) —$OC_{1-3}$ alkyl optionally substituted with 1-3 halogens, (iv) —OH, and (vii) $C_{1-3}$ hydroxyalkyl.
The compounds may be:
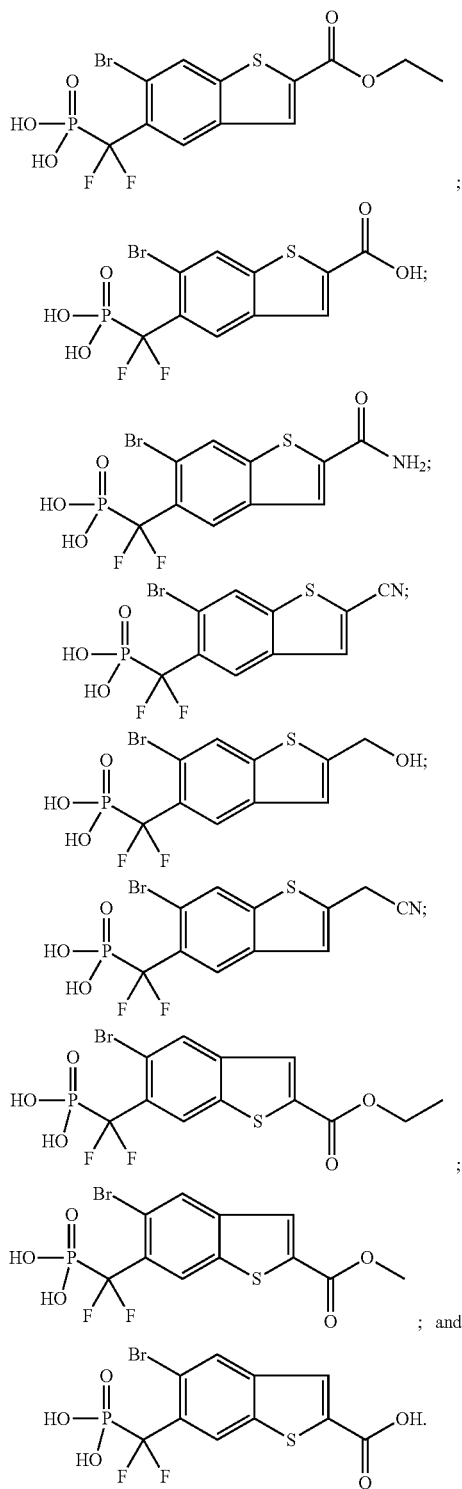
The compound may be selected from the following compounds:
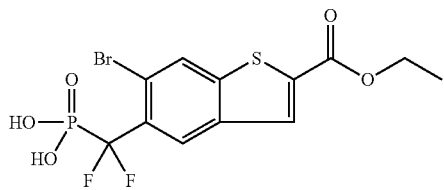
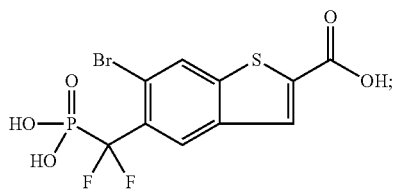
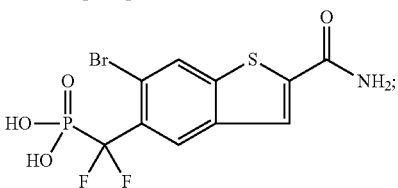
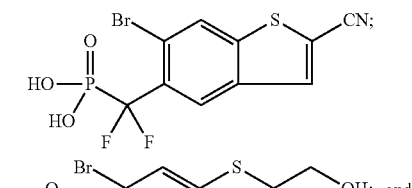
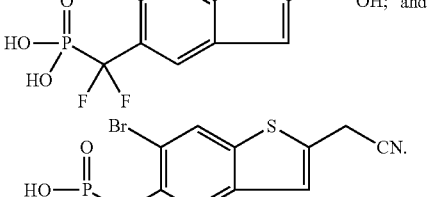
The compound may be selected from the following compounds:
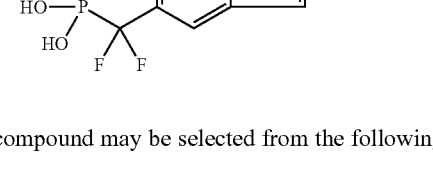
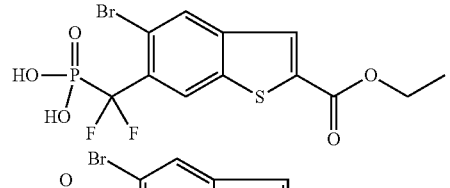
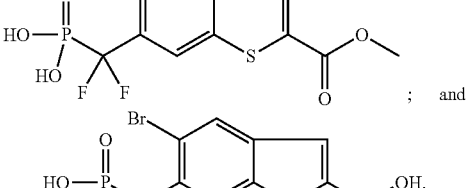
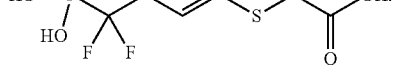

The compound may be

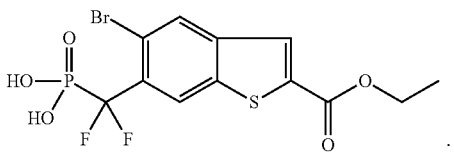 [SMILES: CCOC(=O)c1cc2cc(Br)c(C(F)(F)P(=O)(O)O)cc2s1]

The treating may be under activating conditions, such as the activating conditions described herein above and below.

The ex vivo method may further comprise the step of activating said primary cell before, during or after treatment with said compound of formula I, Ia or Ib.

The treating may be for a time sufficient for expansion, transduction or activation of said isolated primary cell.

The isolated tumor-infiltrating lymphocyte may be harvested from a patient.

The in vitro method may further comprise the step of isolating a primary cell.

According to another embodiment, there may be provided a method of preventing or treating a disease in a patient in need thereof comprising:
  administering a primary cell obtained by the method of the present invention.

The disease may be an infection disease, such as viral, bacteriological, parasitic of fungal diseases; and cancer.

The invention also relates to the use of a compound of structural Formula II, or a pharmaceutically acceptable salts thereof, and stereoisomers thereof:

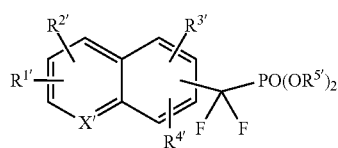

wherein X' is selected from CH and N;
$R^{1'}$ is selected from the group consisting of (a) $C_{1-3}$alkyl optionally substituted with 1-3 halogens and optionally with one group selected from —OH, —$OC_{1-3}$alkyl optionally substituted with 1-3 halogens, —$SO_xC_{1-3}$alkyl, and —CN, (b) —C(═O)H, (c) —C(═O)$C_{1-3}$alkyl optionally substituted with 1-3 halogens, (d) —CN, (e) —HC═NOH, (f) —(CH$_3$)C═NOH, (g) —HC═NO$C_{1-3}$alkyl optionally substituted with 1-3 halogens, (h) —(CH$_3$)C═NO$C_{1-3}$alkyl optionally substituted with 1-3 halogens (i) —C(═O)O$C_{1-3}$alkyl optionally substituted with 1-3 halogens, (j) —C(═O)NHR$^{6'}$, (k) —CH═CH-Phenyl wherein —CH═CH— is optionally substituted with 1-2 substituents independently selected from halogen and $C_{1-2}$alkyl optionally substituted with 1-3 F, (l) —CH$_2$CH$_2$-Phenyl wherein —CH$_2$CH$_2$— is optionally substituted with 1-4 substituents independently selected from halogen and $C_{1-2}$alkyl optionally substituted with 1-3 F, (m) Phenyl, (n) -HET-Phenyl, wherein HET is a 5- or 6-membered heteroaromatic ring containing 1-3 heteroatoms selected from O, N and S, (o) —C≡C-Phenyl, and (p) —CH$_2$-Phenyl, wherein the —CH$_2$— group of —CH$_2$-Phenyl is optionally substituted with 1-2 substituents independently selected from halogen and $C_{1-2}$alkyl optionally substituted with 1-3 F, wherein Phenyl and HET in all occurrences are optionally substituted with 1-3 substituents independently selected from (i) halogen, (ii) —C(═O)O$C_{1-3}$alkyl optionally substituted with 1-3 halogens, (iii) —C(═O)OH (iv) $C_{1-3}$alkyl optionally substituted with 1-3 halogens, (v) —$OC_{1-3}$alkyl optionally substituted with 1-3 halogens, (vi) —SO$_x$Me, and (vii) —SO$_2$NH$_2$;

$R^{6'}$ is selected from the group consisting of H, $C_{1-3}$alkyl optionally substituted with 1-3 halogens, Phenyl, and —CH$_2$-Phenyl, wherein Phenyl in both occurrences is optionally substituted with 1-3 substituents independently selected from (i) halogen, (ii) —C(═O)O$C_{1-3}$alkyl optionally substituted with 1-3 halogens, (iii) —C(═O)OH (iv) $C_{1-3}$alkyl optionally substituted with 1-3 halogens, and (v) —$OC_{1-3}$alkyl optionally substituted with 1-3 halogens;

$R^{2'}$ and $R^{4'}$ are independently selected from H, halogen, —CH$_3$, —CF$_3$, —OCH$_3$, and —OCF$_3$;

$R^{3'}$ is halogen, wherein the halogen is bonded to the fused aromatic ring of Formula II at a position ortho to the —CF$_2$PO(OR$^{5'}$)$_2$ group, each $R^{5'}$ group is independently selected from the group consisting of H and $C_{1-3}$alkyl optionally substituted with 1-3 halogens, and x is 0, 1, or 2.

The compounds of formula II may be

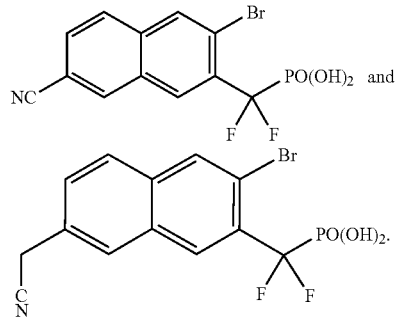

These compounds are inhibitors of TC-PTP and are useful for the ex vivo expansion, transduction and/or activation of tumor-infiltrating lymphocytes (TILs), T cell receptor (TCR) engineered cells, or chimeric antigen receptor (CAR) engineered cells. Injection of these cells into a patient is useful for the treatment of diseases where the patient is unable to mount a sufficient immune response. Such cell products may be useful in the treatment of cancer, AIDS and related medical conditions as well as infectious diseases.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
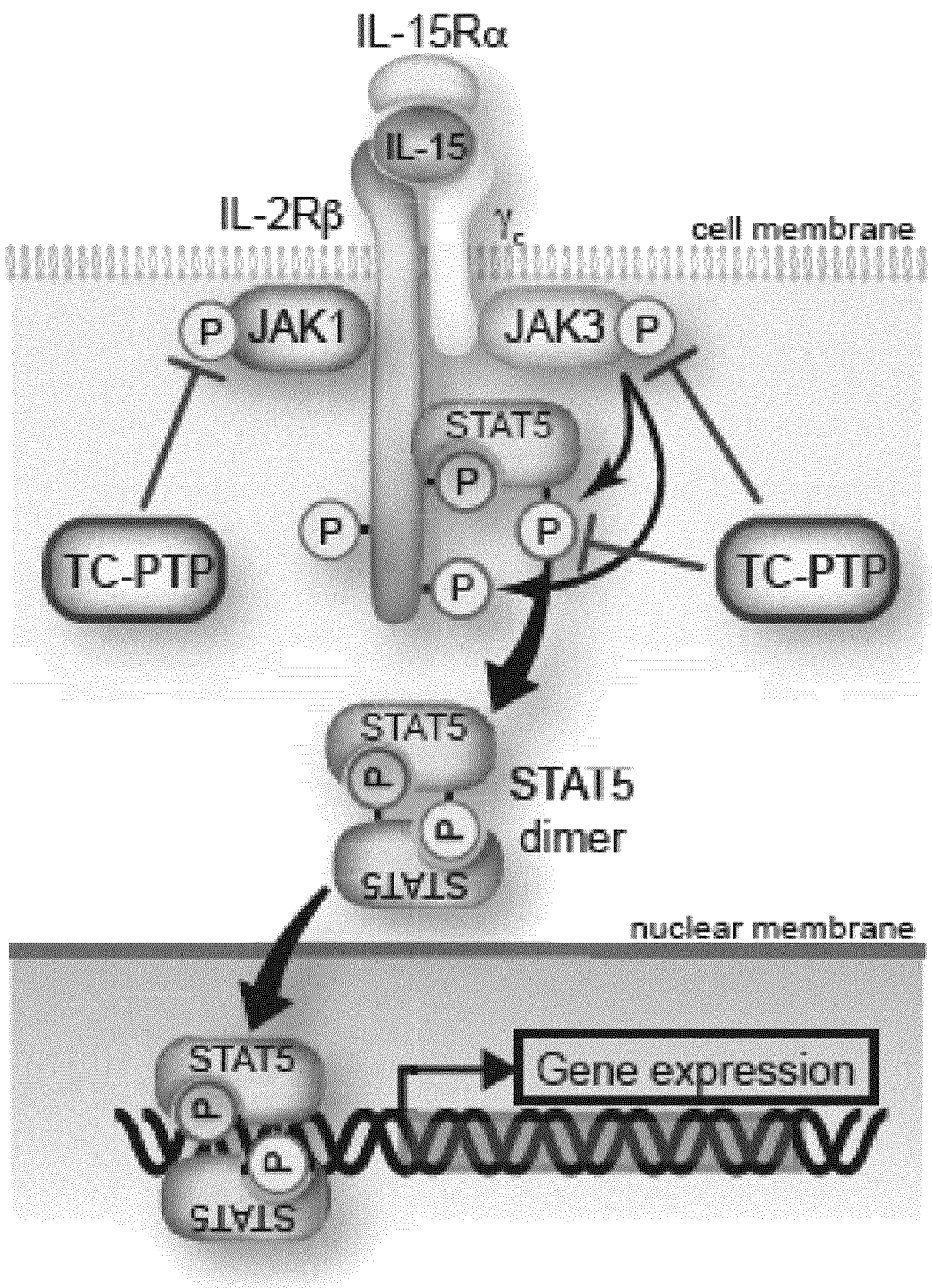
FIG. 1 illustrates the JAK-STAT signal transduction pathway, and the role of TC-PTP therein.

Compounds of Formula I and Formula II are inhibitors of TC-PTP and are useful for the expansion, transduction and/or activation of T cells for treatment of diseases where the patient is unable to mount a sufficient immune response. Such T cell preparations may be useful in the treatment of cancer, viral infections, bacterial infections, fungal infections and parasitic infections.

According to another embodiment, the present invention also relates to methods for ex vivo treatment of T cells harvested from a patient with compounds of Formula I or Formula II in a suitable medium in order to make those cells suitable for injection into a patient.

According to another embodiment, the present invention also relates to methods for ex vivo treatment of T cells with compounds of the present invention at a concentration known to be useful to create a desired change in those cells.

According to another embodiment, the present invention also relates to a method for the incorporation of a compound of the present invention into protocols for the isolation and expansion of tumor-infiltrating lymphocytes (TILs) for use in adoptive cell transfer therapy; or for use in allogenic cell transfer therapy, such as allogenic T cell transfer therapy.

According to another embodiment, the present invention also relates to a method for the incorporation of a compound of the present invention into protocols for the generation and expansion of engineered T cell receptor (TCR)-expressing autologous T cells for use in adoptive cell transfer therapy; or for use in allogenic cell transfer therapy, such as allogenic T cell transfer therapy.

According to another embodiment, the present invention also relates to a methods for the incorporation of a compound of the present invention into protocols for the generation and expansion of chimeric antigen receptor (CAR)-expressing autologous T cells for use in adoptive cell transfer therapy; or for use in allogenic cell transfer therapy, such as allogenic T cell transfer therapy.

According to another embodiment, the present invention also relates to methods for the treatment or control of cancer, and infectious diseases such as viral infections, bacterial infections, fungal infections and parasitic infections and related medical conditions by injecting activated TILs, TCR T cells or CAR-T cells into a patient.

According to another embodiment, the present invention relates to the administration of activated TILs, TCR T cells or CAR-T cells to a patient in need of such therapy by injecting such cells into the bloodstream, into a lymph node, directly into a tumor, or directly into another tissue that has been impacted by the disease the patient is being treated for.

Types of cancer that may be treated by compounds of the present invention include, but are not limited to, prostate cancer, breast cancer, brain cancer, glioma, lung cancer, salivary cancer, stomach cancer, thymic epithelial cancer, thyroid cancer, ovarian cancer, multiple myeloma, leukemia, melanoma, lymphoma, gastric cancer, kidney cancer, pancreatic cancer, bladder cancer, colon cancer and liver cancer.

Types of viral infections that may be treated by the present invention include, but are not limited to, infections caused by cytomegalovirus Epstein-Barr virus, hepatitis B, hepatitis C virus, herpes virus, human immunodeficiency virus, human T lymphotropic virus, lymphocytic choriomeningitis virus, respiratory syncytial virus, and/or rhinovirus.

Types of bacterial infections that may be treated by the present invention include, but are not limited to, infections caused by *Corynebacterium, Enterococcus, Escherichia, Haemophilius, Helicobacter, Legionella, Leptospira, Listeria, Mycobacterium, Neisseria, Porphyromonas, Pseudomonus, Salmonella, Staphylococcus* and *Chlamydia*.

Types of parasitic infections that may be treated by the present invention include, but are not limited to, infections caused by *Schistosoma, Leishmania, Plasmodium, Giardia, Trypanosoma* and *Taenia*.

Types of fungi infections that may be treated by the present invention include, but are not limited to, infections caused by *Aspergillus, Blastomyces, Candida*, Ringworm, and Murcormyces.

According to yet another embodiment, the invention also includes in vitro treatment of primary cells with a compound of Formula I, Formula Ia, and/or Formula Ib or a pharmaceutically acceptable salt thereof, in order to produce activated cells suitable for therapeutic treatment of a patient in need of immunotherapy.

Abbreviations

Abbreviations and terms that are commonly used in the fields of organic chemistry, medicinal chemistry, pharmacology, and medicine and are well known to practitioners in these fields are used herein. Representative abbreviations and definitions are provided below:

Ac is acetyl [$CH_3C(O)$—], $Ac_2O$ is acetic anhydride; ACN is acetonitrile; APC is antigen-presenting cell; Alk is alkyl; Ar is aryl; 9-BBN is 9-borabicyclo[3.3.1]nonane; Bn is benzyl; BOC is tert Butyloxycarbonyl; br is broad; $CH_2Cl_2$ is dichloromethane; d is doublet; DBU is 1,8-diazabicyclo[5.4.0]undec-7-ene; DC is dendritic cell; DEAD is diethyl azodicarboxylate; DIAD is diisopropylazodicarboxylate; DIBAL is diisobutylaluminum hydride; DIPEA is N,N-diisopropylethylamine; DMF is N,N-dimethylformamide; DMSO is dimethyl sulfoxide; EDAC (or EDC) is 1-ethyl-3-[3-(dimethylamino)propyl]-carbodiimide HCl; ESI is electrospray ionization; $Et_3N$ is triethylamine; Et is ethyl; EtOAc is ethyl acetate; EtOH is ethanol; 3-F-Ph is 3-fluorophenyl; h is hours; HATU is O-(7-azabenzotriazol-1-yl)-N,N,N',N'-tetramethyluronium hexafluorophosphate; HOAc is acetic acid; HCl is hydrochloric acid; HOBt is 1-hydroxybenzotriazole; HPLC is high performance liquid chromatography; Hunig's base is diisopropylethylamine; LiOH is lithium hydroxide; LCMS is HPLC with mass Spectral detection; LG is leaving group; m is multiplet; M is molar; mmol is millimole; Me is methyl; MeCN is acetonitrile; MeOH is methanol; MeTHF is 2-methyltetrahydrofuran; $MgSO_4$ is magnesium sulfate; min is minutes; MS is mass spectroscopy; MsCl is methanesulfonyl chloride; MTBE is methyl tert-butyl ether; N is normal; NaHMDS is sodium hexamethyldisiliazide; NaOAc is sodium acetate; NaOH is sodium hydroxide; NaOtBu is sodium tert-butoxide; $Na_2SO_4$ is sodium sulfate; NMO is N-methylmorpholine N oxide; NMP is N Methyl pyrrolidinone; NMR is nuclear magnetic resonance spectroscopy; $Pd(dba)_2$ is tris (dibenzylideneacetone)dipalladium; $PdCl_2(Ph_3P)_2$ is dichlorobis-(triphenylphosphene) palladium; PG Denotes an unspecified protecting group; Ph is phenyl; PhMe is toluene; $PPh_3$ is triphenylphosphine; PMB is para-methoxybenzyl; RT is room temperature; s is singlet; t is triplet; TBAF is tetrabutyl ammonium fluoride; TBS is tert-butyldimethylsilyl; tBu is tert-butyl; Tf is triflate; TFA is trifluoroacetic acid; TFAA is trifluoroacetic anhydride; THF is tetrahydrofuran; TLC is thin layer chromatography; TMEDA is N,N,N',N'-tetramethylethylenediamine; TMS is trimethylsilyl; TPAP is tetrapropylammonium perruthenate.

Definitions

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from C3-10, the term alkyl also includes cycloalkyl groups, and combinations of linear or branched alkyl chains combined with cycloalkyl structures. When no number of carbon atoms is specified, C1-6 is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., C1-6 alkoxy), or any number within this range [i.e., methoxy (MeO—), ethoxy, isopropoxy, etc.].

The term "alkylthio" refers to straight or branched chain alkylsulfides of the number of carbon atoms specified (e.g., C1-6 alkylthio), or any number within this range [i.e., methylthio (MeS—), ethylthio, isopropylthio, etc.].

The term "alkylamino" refers to straight or branched alkylamines of the number of carbon atoms specified (e.g., C1-6 alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., C1-6 alkylsulfonyl), or any number within this range [i.e., methylsulfonyl ($MeSO_2^-$), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl ($MeOCO^-$), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, 2-oxopiperidin-1-yl, 2-oxopyrrolidin-1-yl, 2-oxoazetidin-1-yl, 1,2,4-oxadiazin-5(6H)-one-3-yl, and the like.

"Heteroaryl" means an aromatic or partially aromatic heterocycle that contains at least one ring heteroatom selected from O, S and N. Heteroaryls thus include heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term «composition» as used herein is intended to encompass a product comprising the specified ingredients in the specified amounts, as well as any product which results, directly or indirectly, from combination of the specified ingredients in the specified amounts. Such term in relation to pharmaceutical composition is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

The terms «T cell(s)», «T lymphocyte(s)», «T cell product(s)» as used herein are intended to encompass isolated tumor-infiltrating lymphocyte (TIL), T cell receptor (TCR) engineered cell, and/or chimeric antigen receptor (CAR) engineered cell isolated by the method of the present invention. It also include different memory T cell population such as Stem central memory $T_{SCM}$ cells, Central memory $T_{CM}$ cells and Effector memory TEM cells, that are beneficial to mount and maintain surveillance and Immune response.

The term "activating condition(s)" as used herein is intended to mean culture conditions that are sufficient to activate T cells, and typically include that cytokines and chemokines, a growth factor, or ligands be present in the milieu and induce their cognate receptors in the T cells, a T-cell associated check-point inhibitor, a tumor associated check-point inhibitor, and combinations thereof. For example, IL-2 alone, IL-2 with either IL-21 or IL-7 and/or IL-15 supplemented media will promote T cell proliferation, CD3 and CD28 ligands will promote activation (in soluble or in solid phase), autologous or allogeneic dendritic cells loaded with the specific antigen, any other antigen presenting cell (APC) loaded with the specific antigen, irradiated tumor cells treated or not with proinflammatory cytokines as type 1 and type 2 interferons, and combinations thereof.

The terms "ptpn1" as used herein is intended to mean the tyrosine-protein phosphatase non-receptor type 1, also known as protein-tyrosine phosphatase 1B (PTP1B), and is an enzyme that is the founding member of the protein tyrosine phosphatase (PTP) family. In humans it is encoded by the PTPN1 gene. PTP1B is a negative regulator of the insulin signaling pathway and is considered a promising potential therapeutic target, in particular for treatment of type 2 diabetes. It has also been implicated in the development of breast cancer and has been explored as a potential therapeutic target in that avenue as well.

The terms "ptpn2" as used herein is intended to mean the tyrosine-protein phosphatase non-receptor type 2, also known as T-cell protein-tyrosine phosphatase (TCPTP, TC-PTP), and n humans is encoded by the PTPN2 gene.

Compounds of structural Formula I, structural Formula Ia and/or structural Formula Ib may contain one or more asymmetric centers and can thus occur as racemates and racemic mixtures, single enantiomers, diastereomeric mixtures and individual diastereomers. The present invention is meant to comprehend all such isomeric forms of the compounds of structural Formula I, structural Formula Ia and/or structural Formula Ib.

Compounds of structural Formula I, structural Formula Ia, structural Formula Ib and/or structural Formula II may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural Formula I, structural Formula Ia, structural Formula Ib and/or structural Formula II may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of generic Formula I, Formula Ia, Formula Ib and/or Formula II, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I, Formula Ia, Formula Ib and/or Formula II. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I, Formula Ia, Formula Ib and/or Formula II can be prepared without undue experimentation by conventional techniques well known to those skilled in the art or by processes analogous to those described in the Schemes and Examples herein using appropriate isotopically-enriched reagents and/or intermediates.

Salts and Formulations

It will be understood that, as used herein, references to the compounds of structural Formula I, Formula Ia, Formula Ib and/or Formula II are meant to also include the pharmaceutically acceptable salts, and also salts that are not pharmaceutically acceptable when they are used as precursors to the free compounds or their pharmaceutically acceptable salts or in other synthetic manipulations. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural Formula I, Formula Ia, Formula Ib and/or Formula II are included in the present invention as well.

The pharmaceutical compositions may be in the form of a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Utilities

The compounds specifically exemplified herein exhibit good efficacy in inhibiting the TC-PTP enzyme, as shown by their in vitro assays. The compounds generally have an $IC_{50}$ value of less than 10 μM in the enzyme assay described in the Assays section, and preferably have an $IC_{50}$ value of less than 1 μM.

According to an embodiment, the inhibitors of TC-PTP may improve and may have utility in preventing or treating immunosuppressive diseases.

One aspect of the invention provides a method for the treatment and control of cancer, which comprises administering to a patient in need of such treatment a therapeutically effective amount of TILs, TCR T cells or CAR-T cells that have been activated by a protocol that includes treatment with a compound of Formula I, Formula Ia, Formula Ib, and/or compounds of Formula II.

A second aspect of the invention provides a method for the treatment and control of an infectious disease, which comprises administering to a patient in need of such treatment a therapeutically effective amount of TILs, TCR T cells or CAR-T cells that have been activated by a protocol that includes treatment with a compound of Formula I, Formula Ia, Formula Ib, and/or compounds of Formula II.

A third aspect of the invention provides a method for the treatment and control of immunosuppressive diseases, which comprises administering to a patient in need of such treatment a therapeutically effective amount of TILs, TCR T cells or CAR-T cells that have been activated by a protocol that includes treatment with a compound of Formula I, Formula Ia and/or Formula Ib, and/or compounds of Formula II.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, can be treated. However, the method can also be practiced in other species, such as avian species (e.g., chickens).

For in vitro use, the compounds of Formula I, Formula Ia, Formula Ib or Formula II can be administered as a solution in water, DMSO or a mixture of water and DMSO, to a suspension of cells in a typical media such that the final concentration is about 1 nM to about 500 μM.

Kits

Compounds of Formula I, Formula Ia, Formula Ib, and Formula II when being used for in vitro purposes, may be packaged for use as a crystalline solid, an amorphous solid or a lyophilized powder. Suitable quantities range from about 0.1 mg to 1 g. Ideally, the compound is packaged in a container to which a suitable solvent can be added to achieve the desired concentration of solution. Alternatively, the compound may be packaged as an aqueous solution at a fixed concentration, or as a solution in a water-soluble organic solvent at a fixed concentration. Suitable organic solvents may include DMSO, methanol, ethanol or acetonitrile, or mixtures of these solvents with water. Suitable concentrations are about 0.1 mM to about 25 mM.

The present invention includes kits encompassing the compounds of Formula I, Formula Ia, Formula Ib and/or Formula II, and instructions on how to use said compounds. According to an embodiment, the kit may also include appropriate cytokines, media and/or stimulatory compounds. The kit will allow a patient's cells to be conveniently activated, isolated and reinjected in a clinical setting. This treatment can be optimized to work best with current clinical therapeutic standards.

The T cells activated with a compound of Formula I, Formula Ia, Formula Ib and/or Formula II may be administered to a patient in need of immunotherapy in one or more injections. The frequency of injection and the intervals between injections will be adjusted to maximize the therapeutic response. For example, injections may occur once, twice, or more times daily, once, twice, or more times weekly, biweekly, monthly or bimonthly or at any other intervals deemed most suitable to the therapeutic benefit of the patient.

Combination Therapy

A patient in need of immunotherapy may be treated with T cells activated with a compound of Formula I, Formula Ia, Formula Ib and/or Formula II contemporaneously with other treatments known to the medical practitioner. The use of such multiple treatments may be particularly advantageous to the patient. Such treatments may include, but are not limited to, surgical resection, radiation, chemotherapy, targeted therapy and other types of immunotherapy. Chemotherapy agents that may be used include:

a) cytotoxic agents such as taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof;

b) antimetabolites such as methotrexate, 6-mercaptopurine, 6-thioguanine, gemcitabine, cytarabine, 5-fluorouracil decarbazine;

c) alkylating agents such as mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin;

d) anthracyclines such as daunorubicin and doxorubicin;

e) antibiotics such as dactinomycin, bleomycin, mithramycin, and anthramycin (AMC);

f) anti-mitotic agents such as vincristine and vinblastine;

g) targeted therapies that may be used include, but they are not limited to: hormone therapies (such as degarelix, a luteinizing hormone-releasing hormone (LHRH) antagonist that reduces testosterone levels in prostate cancer), signal transduction inhibitors (such as imatinib, trastuzumab, PARPi, and CDKi), as well as gene expression modulators (for example the HDAC inhibitors panobinostat and belinostat), apoptosis inducers (such as recombinant human TNF-related apoptosis-inducing ligand (TRAIL)) and angiogenesis inhibitors (such as sorafenib, sunitinib, pazopanib and everolimus);

h) Immunotherapy agents that may be used include: monoclonal antibodies treatment (anti-CTLA4, anti-PD1, anti-PD-L1, anti-LAG3, anti-KIR), and dendritic cell (DC) vaccines.

Multiple treatments may also include checkpoint inhibitors or modulator of immunotherapy.

The most recognized checkpoint inhibitors are anti-PD1 and anti-CTLA4, yet in the interaction of dendritic cells with tumors cells, effector T-cells, and other immune cells, a number of protein interactions favoring or inhibiting the recognition and killing of tumor cells has been identified. For example, a dozen of those interactions have been reported to affect DC and tumors cells (K. Palucka and J. Banchereau, Nature Reviews Cancer 12:265-277). Hence the technology described herein may be conjugated to many of those additional immunotherapy technologies currently in development.

Assays for Measuring Biological Activity

Activity of the compounds of this application may be evaluated using the following assays for TC-PTP-inhibiting activity. Compounds of Formula I will have activities of <10 µM in this assay, and preferably, activity of <1 µM.

1) Enzyme Assay for TC-PTP
Assay buffer: 50 mM Bis-Tris (pH=6.3)
  2 mM EDTA
  5 mM N,N'-dimethyl-N,N'-bis(mercaptoacetyl)hydrazine (DMH)
Substrate: 10 mM fluorescein diphosphate (FDP) store at −20° C. (also can use 10 mM DiFMUP)
Enzyme dilution buffer: 50 mM Bis-Tris (pH=6.3)
  2 mM EDTA
  5 mM DMH
  20% (v/v) glycerol
  0.01% Triton X-100

The assay was carried out at room temperature in 96 well plates. The reaction mixture in 170 µl contained 50 mM Bis-Tris (pH=6.3), 2 mM EDTA, 5 mM N,N'-dimethyl-N,N'bis(mercaptoacetyl)hydrazine (DMH) and 10 µM fluorescein diphosphare (FDP) or 6,8-difluoro-4-methylumbelliferyl phosphate (DiFMUP). 10 µl of 10 concentrations (serial dilution) of the test compound (inhibitor) dissolved in DMSO or DMSO alone for control was added to each well and the plate was mixed for 2 min. The reaction was initiated by adding 20 µl of diluted TC-PTP (50 nM for FDP, 0.5 nM for DiFMUP in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) or 6,8-difluoro-7-hydroxyl-4-coumarin (DiFMU) continuously for 15-30 min, using the Spectromax Gemini fluorescent plate reader (Molecular probes) with excitation at 440 nm and emission at 530 nm (cutoff filter at 525 nm) for FDP and excitation at 360 nm and emission at 450 nm (cutoff filter at 435 nm) for DiFMUP. All the assays were done at least in duplicate. The initial rate of FMP or DiFMU formation is plotted against the concentration of inhibitor and the data was fitted to 4-parameter equation and the inflection point of the fit is the $IC_{50}$.

2) Generation of Mouse CD8 Memory-Phenotype Culture Protocol:
Day 0:
  Spleens were isolated from TC-PTP$^{+/+}$ or TC-PTP$^{-/-}$ mice and placed in 5 mL of RPMI/5% FCS in a 6-well plate
  cell strainers were inserted into 50 mL conical tubes
  Each spleen was placed on a 40µ cell strainer inserted in a 50 mL conical tube.
  Spleens were dissociated with a 3 mL syringe plunger
  Each cell strainer was then rinsed with 5 mL of RPMI/5% FCS
  Cell strainers were then removed and conical tubes capped
  Cell suspensions were spun at 1200 rpm for 5 minutes
  Supernatant was aspirated and cells were resuspended in 5 mL of Red Blood Cell Lysis Buffer (Sigma-Aldrich, R7757) and incubated for 5 minutes at room temperature
  10 mL of RPMI/5% FCS was added and cells were spun down at 1200 rpm for 5 minutes
  Supernatant was aspirated and the cell pellet resuspended in 10 mL of RPMI/5% FCS and cells counted
  T cells were enriched using EasySep STEMCell T cell enrichment kit (cat #19751):
    Cells were resuspended at a concentration of 1×10$^8$ cells/mL in PBS/2% FCS and transferred to a 5 mL polystyrene tube
    Normal rat serum was added at 50 µL/mL of cells
    The Mouse T cell Enrichment cocktail was added at 50 µL/mL of cells, mixed by pipetting and incubated for 15 minutes at 4° C.
    The Biotin Selection Cocktail was added at 100 µL/mL of cells, mixed by pipetting and incubated for 15 minutes at 4° C.
    Magnetic Particles were vortexed for 30 seconds
    Magnetic Particles were added at 75 µL/mL of cells, mixed by pipetting and incubated for 5 minutes at 4° C.
    The cell suspension was then brought up to a total volume of 2.5 mL by adding PBS/2% FCS.
    Cells were mixed by pipetting up and down 2-3 times and the tube was placed in the magnet and set aside for 5 minutes
    The magnet was then picked up and cells were poured out in one continuous motion. The magnet and tube were left inverted for 2-3 seconds and then returned to the upright position
    Enriched T cells were then washed with 5 mL PBS/2% FCS
  Purified T cells were plated at a density of 2×10$^6$ cells/mL/well in a 24-well plate that had been pre-coated with anti-CD3 and anti-CD28 antibodies. Plates were incubated for 2 days at 37° C.
  1×10$^6$ cells were reserved for FACS staining for CD8, CD69, CD44 and CD62L to verify that T cells are naïve.
    Ab coating of 24-well plates:
      Sterile antibody stocks of anti-CD28 and anti-CD3 were used
      Antibodies were dilute to 10 µg/ml (anti-CD28) and 1 µg/ml (anti-CD3) in antibody coating buffer (0.05M Tris pH 9.2, filtered)

500 μL of diluted antibody was aliquoted per well of a 24-well plate and the plate was incubated overnight at 37° C.

Remaining antibody was removed by aspiration, and wells were rinsed 3 times with 1 mL of PBS, ensuring the wells did not dry Day 2:
  Cells were harvested by pipetting and transferring to a 15 mL conical tube
  Cells were washed 2 times with 5 mL of PBS
  Cells were resuspended in 5 mL of PBS and counted
  $1 \times 10^6$ cells were FACS stained for CD8, CD69, CD44 and CD62L to verify activation
  Cells were plated at a density of $1 \times 10^6$ cells/mL/well in T cell media supplemented with recombinant IL-15 (Peprotech, 210-15)
    T cell media: RPMI,
      10% FCS,
      Pen/Strep (100 units/ml),
      Non-essential amino acids (0.1 mM/mL for each amino acid),
      Sodium pyruvate (1 mM),
      β-mercaptoethanol (0.055 mM)

Day 4-10:
  Every 2 days, cells were harvested, washed with PBS, counted and replated at $1 \times 10^6$ cells/mL, in T cell media supplemented with fresh recombinant IL-15

Day 12:
  Cells were harvested, washed and counted
  Cells were FACS stained for CD8, CD44, CD69, CD62L to verify purity of memory-phenotype CD8 cells.

3) Characterization of TC-PTP Deficient CD8 Memory T Cells by Western

On day 12 of culture, CD8 memory cells were harvested and pelleted at 1200 rpm for 5 minutes. Cells were washed with 10 mL of ice-cold PBS. The supernatants were aspirated and the cell pellets were frozen at −80° C. After thawing, the cell pellets were lysed in RIPA buffer and analyzed by Western blot on SDS-PAGE.

4) Seahorse Assay:

The bioenergetics of the differentiated memory-phenotype CD8 T cells were measured in the basal state following the protocol detailed in the following reference:

*Current Protocols in Immunology. UNIT 3.16B. Measuring Bioenergetics in T Cells Using a Seahorse Extracellular Flux Analyzer.* Gerritje J. W. van der Windt, Chih-Hao Chang, Erika L. Pearce. Published Online: 1 Apr. 2016

5) Isolation of Mouse Thymus, Spleen and Lymph Node Mononuclear Cells

To isolate thymus, spleen and lymph node mononuclear cells, mice are euthanize by inhalation of $CO_2$, followed by neck dislocation. The required organs are obtained and placed in a 60 mm dish with 4 ml of ice-cold PBS+2% FBS over ice. The organ is gently mashed up using a 40 μm cell strainer (BD 352340) and the piston of a 1 ml syringe until the capsule of the cell strainer is empty. The cells suspension is recovered and used for experiments.

6) Isolation of Mouse Peripheral Blood Mononuclear Cells (PBMC)

4 ml of sterile lympholyte-M (Cedarlane CL5030) at room temperature are added to a 15 ml tube. The cell suspension is carefully layered over the lympholyte-M and spun at 800×g for 15 min at room temperature, with the brake of the centrifuge disabled. After spinning, the white interphase between the lympholyte-M and the cell media "buffy coat" is carefully taken and transferred to a 15 ml tube with 10 ml of culture media. This is then spun at 300×g for 5 min at room temperature. The cells are resuspended in complete RPMI, and are ready for use.

7) Isolation of Mouse CD8 T Cells

To isolate mouse CD8 cells the EasySep™ Mouse $CD8^+$ T Cell Enrichment Kit (Catalog #19753) was used following the manufacturer instructions as follow. This procedure is for processing 100 μL-2.5 mL of sample (up to $2.5 \times 10^8$ cells). Prepare a single cell suspension at a concentration of $1 \times 10^8$ cells/mL in PBS-2% FBS. For samples containing $10^7$ cells or fewer, resuspend in 100 μL. Cells must be placed in a 5 mL (12×75 mm) polystyrene tube to properly fit into the Purple EasySep® Magnet. Falcon™ 5 mL Polystyrene Round-Bottom Tubes (BD Biosciences, Catalog #352058) are recommended. CD8α PE Labeling Reagent is added at 50 μL/mL of cells (e.g. for 2 mL of cells, add 100 μL of labeling reagent). After mixing well, incubate at room temperature (15-25° C.) for 15 minutes. EasySep® PE Selection Cocktail is added at 100 μL/mL of cells (e.g. for 2 mL of cells, add 200 μL of cocktail). Mix well and incubate at room temperature (15-25° C.) for 15 minutes. EasySep® Magnetic Nanoparticles are mixed by pipetting vigorously up and down more than 5 times to ensure that they are in a uniform suspension. The nanoparticles are added at 50 μL/mL of cells (e.g. for 2 mL of cells, add 100 μL of nanoparticles). After mixing well, the cells are incubated at room temperature (15-25° C.) for 10 minutes. The cell suspension is brought to a total volume of 2.5 mL by adding recommended medium. The cells are mixed in the tube by gently pipetting up and down 2-3 times. The tube is place (without cap) into the magnet and set aside for 5 minutes. The magnet is picked up and in one continuous motion the magnet and tube are inverted, pouring off the supernatant fraction. The magnetically labeled cells will remain inside the tube, held by the magnetic field of the EasySep® Magnet. The magnet and tube are held in inverted position for 2-3 seconds, then returned to upright position. Any drops that may remain hanging from the mouth of the tube should not be shaken or blotted off. The tube is then removed from the magnet and 2.5 mL of recommended medium added. The cell suspension is mixed gently by gently pipetting up and down 2-3 times. The tube is placed back in the magnet and set aside for 5 minutes. Repeat the magnet and cell resuspension steps, and then the cell resuspension step once more, for a total of 3×5-minute separations in the magnet. Remove tube from magnet and resuspend cells in an appropriate amount of desired medium. The positively selected cells are now ready for use.

8) Stimulation of Mouse CD8 T Cells

2 μg/ml of 145-2C11 Hamster anti-Mouse CD3e in 300 μl of PBS are plated in 24 flat bottom well non-TC treated plates. Incubate O/N at 4° C. CD8 T cells from spleens of 8-12 weeks old OT-1 transgenic mice are isolated. $4 \times 10^5$ cells/ml are counted and resuspended in complete RPMI (RPMI+10% FBS heat inactivated at 55° C. for 45 min+Pen/Strep+55 μM β-Mercaptoethanol). The following 2× solutions are prepared:
  a. Anti-Mouse CD28 10 μg/ml 40 U/ml rmIL-2. (40 ml)
  b. 5 ml Anti-Mouse CD28 10 μg/ml 40 U/ml rmIL-2 and 20 μM K884.

0.5 ml of 2× solution is added to the corresponding wells. Incubate for 4-8 days. Every 2 days add inhibitor to the corresponding concentration. When the cells are confluent, expand to 6 cm tissue culture plates adding 4 ml of complete RPMI+20 U/ml of IL-2 and in b add 10 μM K884.

9) Cytotoxicity Experiments 3 days before the experiment thaw a new vial of EG.7 cells. After 24 h in culture, the cells are resuspended at $5 \times 10^4$ and 100 U/ml of IFN-γ is added. The day of the experiment, the EG.7 cells are harvested, washed once with HBSS. The EG.7 cells are resuspended at $10^6$/ml in HBSS and 10 μM Calcein-AM added. The cells are incubated at 37° C. for 1 hr in the dark, washed twice with complete RPMI and counted. They are then resuspend at $3 \times 10^5$/ml.

The following wells from a $0.75 \times 10^6$/ml suspension of the CD8 (Effector) cells to have different effector to target ratios are prepared in duplicate. Before plating the effector cells, RPMI complete is added, 50 μl to the 5:1 ratio wells and 90 μl to the 1:1 ratio wells.

$75 \times 10^3$ (100 μl) 25:1 ratio.
Dilute the suspension 1:2.5 volumes:
$30 \times 10^3$ (100 μl) 10:1 ratio.
$15 \times 10^3$ (50 μl) 5:1 ratio.
$3 \times 10^3$ (10 μl) 1:1 ratio.

Prepare at least 2 wells with 100 μl of RPMI complete. 100 μl of EG.7 (Target) cells is added and spin at 400×g for 2 minutes, RT. Incubate for 5 h at 37° C., 5% $CO_2$ and in the dark. At the end of the incubation spin 5 min at 400×g, RT. 100 μl of supernatant is harvested from each well and transferred to a black 96 flat bottomed well plates.

For Controls: Background fluorescence (BF): Harvest 100 μl supernatant from control wells. Absolut fluorescence (AF): Add 100 μl of methanol to the control wells harvested for background. Resuspend with vigorous pipetting and harvest 100 μl of the suspension.

Calculate the specific cell lysis as follows:

$$\text{Specific cell lysis} = ((\text{Sample} - \text{BF})/(\text{AF} - \text{BF})) \times 100$$

10) Flow Cytometry
1. Cell Activation
   a. Wash cells with 1 ml of culture medium;
   b. Centrifuge cells for 5 min at 300 g;
   c. Resuspend cells in culture medium;
   d. Prepare 2× solutions (negative control with only culture medium, Positive condition with 50 ng/mL of PMA and 500 ng/mL of Ionomycin);
   e. Plate 100 μL of cell suspension in 96 well plates (U-bottom);
   f. Add 100 μL of 2× solutions in appropriate wells;
   g. Incubate 4 hours at 37 C, 5% $CO_2$.
2. Extracellular Staining
   a. Record cell quantity transfers per tube;
   b. Wash cells with 1 mL of PBS+2% FBS;
   c. Centrifuge cells for 5 min at 300 g;
   d. Empty tubes by inversion;
   e. Add the antibodies for extracellular staining;
   f. Incubate 20 min at 4° C.;
   g. Wash cells with 1 mL of PBS+2% FBS;
   h. Centrifuge cells for 5 min at 300 g;
   i. Empty tubes by inversion;
   j. Ressuspend cells in 100 μL fixation/permeabilisation buffer (eBioscience, #00-5223-56, 1 volume of concentrate buffer+3 volumes of diluent buffer)
   k. Incubate 30 min at room temperature or overnight at 4° C.
3. Intracellular Staining
   a. Wash cells with 1 mL of permeabilization buffer (eBioscience, #00-8333-56, dilution 1/10 in $ddH_2O$);
   b. Centrifuge cells for 5 min at 300 g;
   c. Empty tubes by inversion;
   d. Add the intracellular antibodies;
   e. Incubate 1 hour at 4° C.;
   f. Wash cells with 1 mL of permeabilization buffer;
   g. Centrifuge cells for 5 min at 300 g;
   h. Empty tubes by inversion;
   i. Keep tubes at 4° C. shelter from light
4. Human PBMC Isolation by Ficoll
   a. Prepare 50 ml tubes;
   b. Transfer blood into 50 ml tubes, with maximum of 17.5 ml per tube;
   c. Add sterile PBS to dilute blood to reach 35 ml;
   d. Use a dropped-in Pasteur pipet used as a tunnel; add 15 ml of Ficoll;
   e. Gently install the tubes and centrifuge at 1000 g for 20 min, RT without brakes;
   f. Using a 25 ml pipet, harvest the interface ring of PBMC without too much Ficoll and transfer into a 50 ml tube (maximum 15 ml per tube);
   g. Wash PBMC with at least 3 volumes of RPMI or PBS and centrifuge 300 g 10 min at 4° C.;
   h. Wash again PBMC with at least 3 volumes of RPMI and centrifuge 300 g 10 min at 4° C.;
   i. Discard supernatant and resuspend in RPMI
   j. Count PBMC.
5. Human T cell enrichment (EasySep™ Human T Cell Isolation Kit, #17951, StemCell Technologies™)
   a. Prepare a PBMC suspension in PBS 2% FBS 1 mM EDTA at $5 \times 10^7$ cells/mL in 5 mL round-bottom tube;
   b. Add Isolation cocktail, 50 μL/mL of sample;
   c. Mix and incubate at room temperature, 5 min;
   d. Vortex magnetic beads full speed 30 seconds;
   e. Add magnetic beads, 50 μL/mL of sample. Mix and incubate at room temperature, 10 min;
   f. Fill the 5 mL tube up to 2.5 mL with PBS 2% FBS 1 mM EDTA solution;
   g. Put the 5 mL tube into the magnet and incubate 5 min;
   h. In one continuous movement, transfer the cell suspension into a new tube;
   i. Wash cell suspension with cell culture medium and centrifuge 5 min, 300 g;
   j. Count cells.

11) Treatment of Human T Cells WITH K884

Stimulation of cells with CD3 and CD28 stimulation, with or without cytokines was performed as follows. CD3 coating is introduced in 96 well plates having a U bottom, by introducing a final concentration of 5 μg/mL CD3 in PBS. 50 μl/well (from a stock 1 mg/mL), and incubated for 1.5 h at 37° C., followed by 3 washes with 200 μl PBS. Next, CD28 is added in the culture medium (from a 1000× stock for a final concentration of 1 μg/mL. Treatment with cytokines may be performed by adding IL2 (50 U/mL), IL7 (10 ng/mL), and IL15 (5 ng/mL), as required. Treatment with K884 is performed by adding 10 μM of the compound to the medium. The culture medium is changed every 2-3 days by replacing half the culture medium with fresh culture medium containing the K884 compound and/or cytokines, as required. The cells are maintained up to 14 days in culture for differentiation characterization. Phenotyping of the cells is performed at days 7 and 14 with the following differentiation markers: CD45RO, CD45RA, CD62L, and CCR7. Functionality testing is performed at day 14 by testing for the secretion of TNFα and IFNγ following PMA Ionomycin restimulation.

Preparation of Compounds of the Invention

Synthetic methods for preparing the compounds of the present invention can be found in WO 2015/127548 and WO 2008/089581.

The following Examples are provided to illustrate the invention and are not to be construed as limiting the invention in any manner. The scope of the invention is defined by the appended claims.

Example 1

((6-BROMO-2-(ETHOXYCARBONYL)BENZO[B]THIOPHEN-5-YL)DIFLUOROMETHYL)PHOSPHONATE

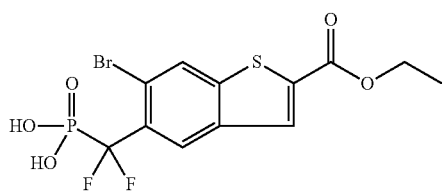

This compound was prepared as described in WO 2015/127548. This compound is also referred to herein as K884.

Example 2

6-BROMO-5-(DIFLUORO(PHOSPHONATO)METHYL)BENZO[B]THIOPHENE-2-CARBOXYLATE

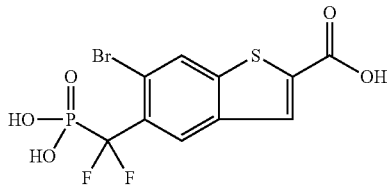 [SMILES: O=C(O)c1cc2cc(C(F)(F)P(=O)(O)O)c(Br)cc2s1]

This compound was prepared as described in WO 2015/127548. This compound is also referred to herein as K882.

Example 3

((6-BROMO-2-CARBAMOYLBENZO[B]THIOPHEN-5-YL)DIFLUOROMETHYL)PHOSPHONATE

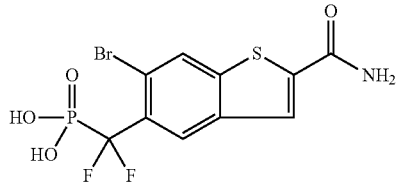 [SMILES: NC(=O)c1cc2cc(C(F)(F)P(=O)(O)O)c(Br)cc2s1]

This compound was prepared as described in WO 2015/127548.

Example 4

((6-BROMO-2-CYANOBENZO[B]THIOPHEN-5-YL)DIFLUOROMETHYL)PHOSPHONATE

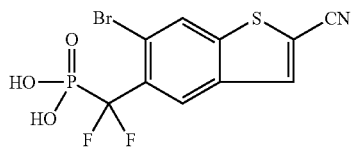

This compound was prepared as described in WO 2015/127548.

Example 5

((6-BROMO-2-(HYDROXYMETHYL)BENZO[B]THIOPHEN-5-YL)DIFLUOROMETHYL)PHOSPHONATE

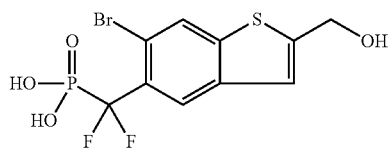 [SMILES: N#CCc1cc2cc(C(F)(F)P(=O)(O)O)c(Br)cc2s1]

This compound was prepared as described in WO 2015/127548.

Example 6

((6-BROMO-2-(CYANOMETHYL)BENZO[B]THIOPHEN-5-YL)DIFLUOROMETHYL)PHOSPHONATE

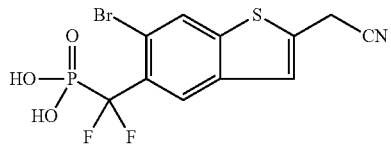

This compound was prepared as described in WO 2015/127548.

Example 7

((5-BROMO-2-(ETHOXYCARBONYL)BENZO[B]THIOPHEN-6-YL)DIFLUOROMETHYL)PHOSPHONATE

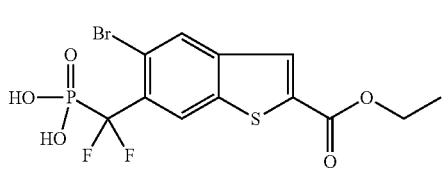 [SMILES: CCOC(=O)c1cc2cc(Br)c(C(F)(F)P(=O)(O)O)cc2s1]

This compound was prepared as described in WO 2015/127548. This compound is also referred to herein as K885.

Example 8

((5-BROMO-2-(METHOXYCARBONYL)BENZO[B]THIOPHEN-6-YL)DIFLUOROMETHYL)PHOSPHONATE

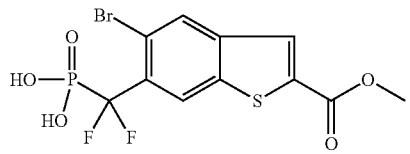 [SMILES: COC(=O)c1cc2cc(Br)c(C(F)(F)P(=O)(O)O)cc2s1]

This compound was prepared as described in WO 2015/127548.

Example 9

((5-BROMO-2-(CARBOXY)BENZO[B]THIOPHEN-6-YL)DIFLUOROMETHYL)PHOSPHONATE

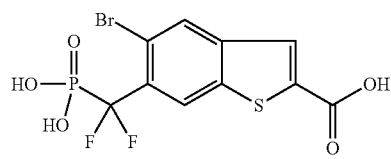 [SMILES: O=C(O)c1cc2cc(Br)c(C(F)(F)P(=O)(O)O)cc2s1]

This compound was prepared as described in WO 2015/127548.

Example 10

[(3-BROMO-7-CYANO-2-NAPHTHYL)(DIFLUORO)METHYL]PHOSPHONATE

This compound was prepared as described in WO 2008/089581.

Example 11

[3-BROMO-7-(CYANOMETHYL)-2-NAPHTHYL](DIFLUORO)METHYL PHOSPHONIC ACID

This compound was prepared as described in WO 2008/089581.

Example 12

Enzyme Assay Data on TC-PTP

When tested against TC-PTP, the following inhibitions of enzymatic activity were observed:

| Compound | IC$_{50}$ (µM) |
|---|---|
| Ex. 1 | 0.45 |
| Ex. 2 | 0.26 |
| Ex. 3 | 0.28 |
| Ex. 4 | 1.2 |
| Ex. 5 | 1.5 |
| Ex. 6 | 0.37 |
| Ex. 7 | 0.74 |
| Ex. 8 | 2.9 |
| Ex. 9 | 0.17 |
| Ex. 10 | 0.49 |

Example 13

FACS Characterization of T Cells

Figure 2:
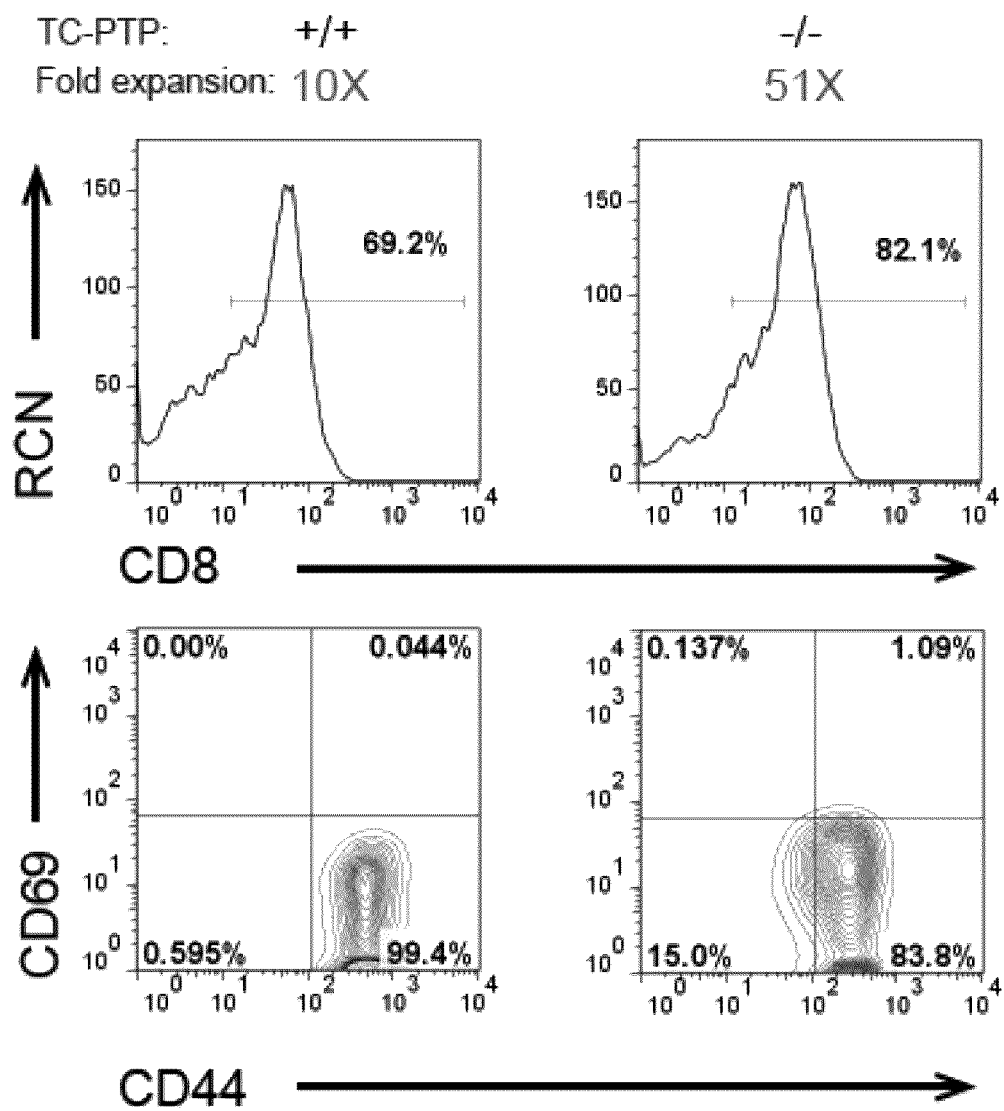
FIG. 2 illustrates representative contour plots of wild-type (+/+) and knock-out (−/−) TC-PTP in vitro differentiated memory CD8+ T cells.

FIG. 2 shows representative contour plots of wild-type (+/+) and knock-out (−/−) TC-PTP in vitro differentiated memory CD8 T cells. Percentages indicate the frequency of cells within defined gates. The fold expansion of CD8 T cells following 6 days of culture in the presence of IL-15 is indicated. RCN=Relative Cell Number.

Example 14

Western Blot Analysis of T Cells

Figure 3:
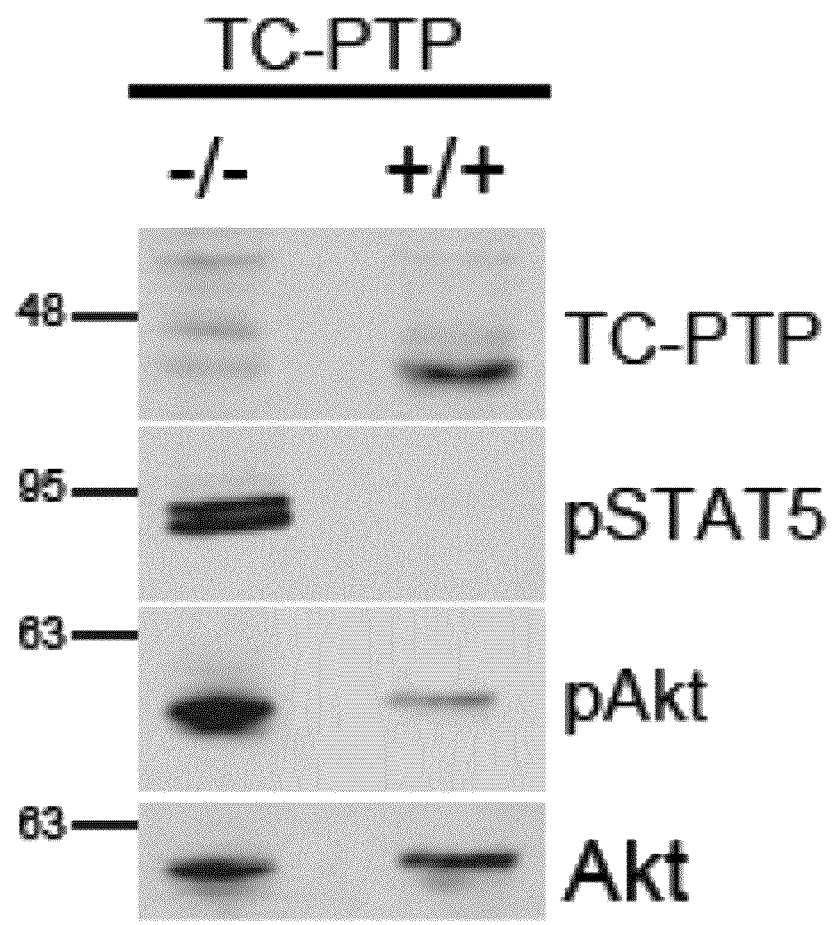
FIG. 3 illustrates Western blot analysis of total cell lysates generated from TC-PTP$^{+/+}$ and TC-PTP$^{-/-}$ in vitro differentiated memory CD8+ T cells.

FIG. 3 shows the Western blot analysis of total cell lysates generated from TC-PTP$^{+/+}$ and TC-PTP$^{−/−}$ in vitro differentiated memory CD8 T cells were resolved by SDS-PAGE. Membranes were probed as indicated.

Example 15

Seahorse Analysis of T Cells

Figure 4:
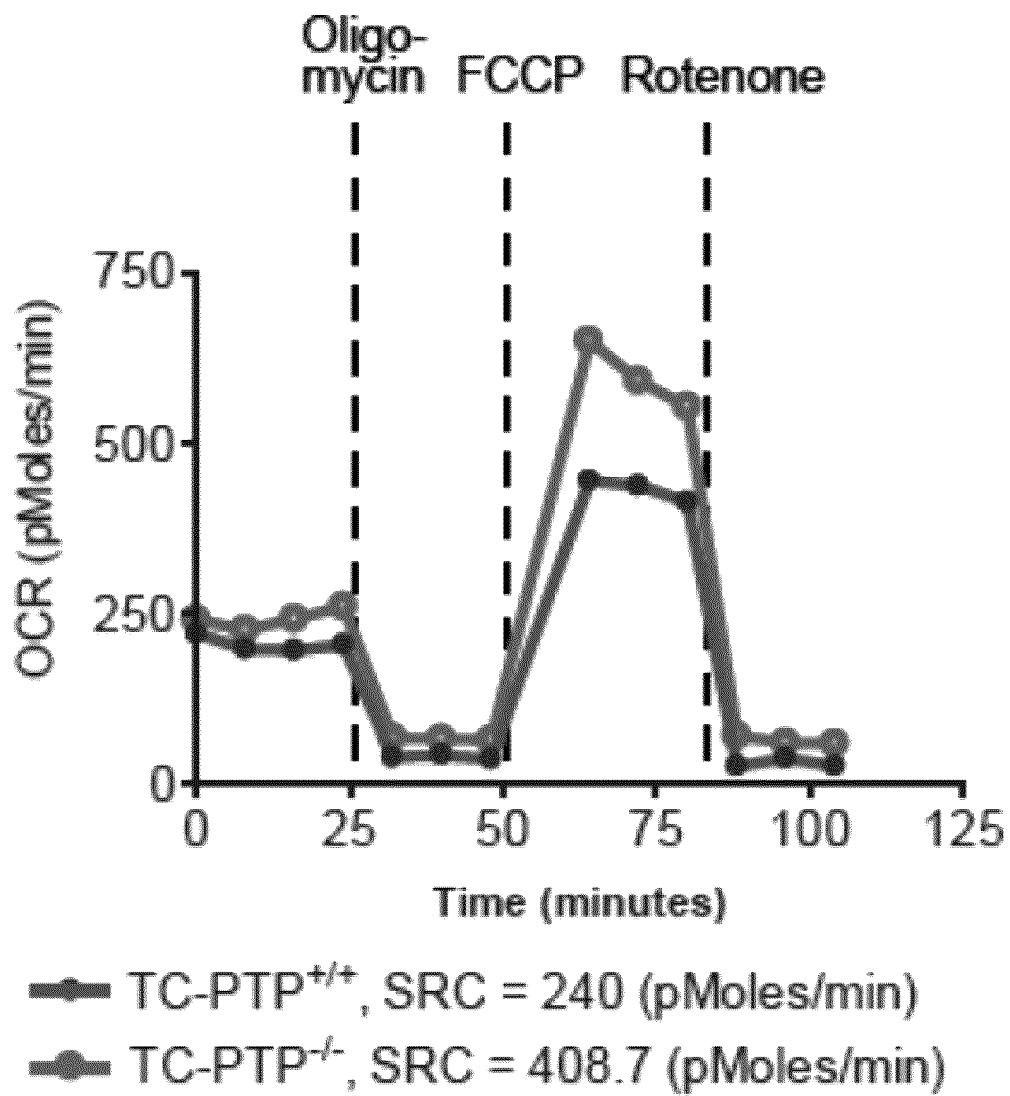
FIG. 4 illustrates an experiment quantifying the $O_2$ consumption rates (OCR) of in vitro generated TC-PTP$^{+/+}$ and TC-PTP$^{-/-}$ memory CD8+ T cells in response to indicated mitochondrial inhibitors.

FIG. 4 shows a representative experiment quantifying the O$_2$ consumption rates (OCR) of in vitro generated TC-PTP$^{+/+}$ and TC-PTP$^{−/−}$ memory CD8 T cells in response to indicated mitochondrial inhibitors. The spare respiratory capacity (SRC) is calculated as the difference between the maximal OCR following FCCP treatment and the basal OCR.

Example 16

Results

Figure 5A:
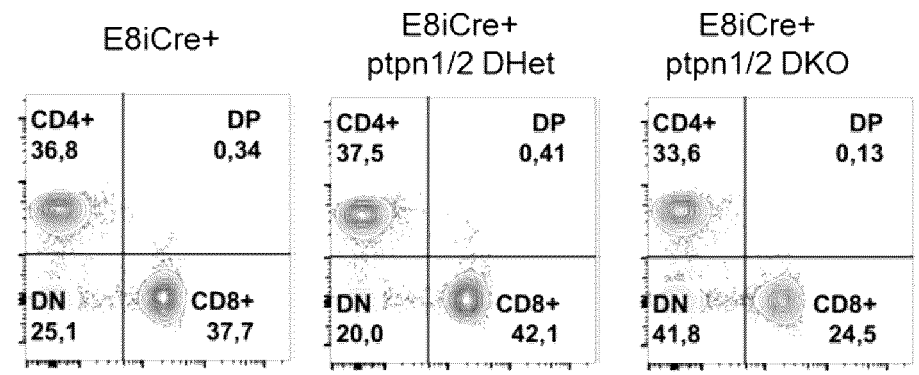
FIG. 5A illustrates CD4 and CD8 T cell populations in lymph nodes of naïve ptpn$^{fl/fl}$/ptpn2$^{fl/fl}$E8iCre mice. Flow cytometric analysis of lymph node cell suspensions stained with antibodies for CD4, CD8, CD62L and CD44. Shown are representative plots of Cre+ controls (ptpn1$^{wt/wt}$/ptpn2$^{wt/wt}$;E8iCre), double heterozygous (DHet) (ptpn1$^{wt/fl}$/ptpn2$^{wt/fl}$;E8iCre) and double knockouts (DKO) (ptpn1$^{fl/fl}$/ptpn2$^{fl/fl}$;E8iCre) are shown.
Figure 5B:
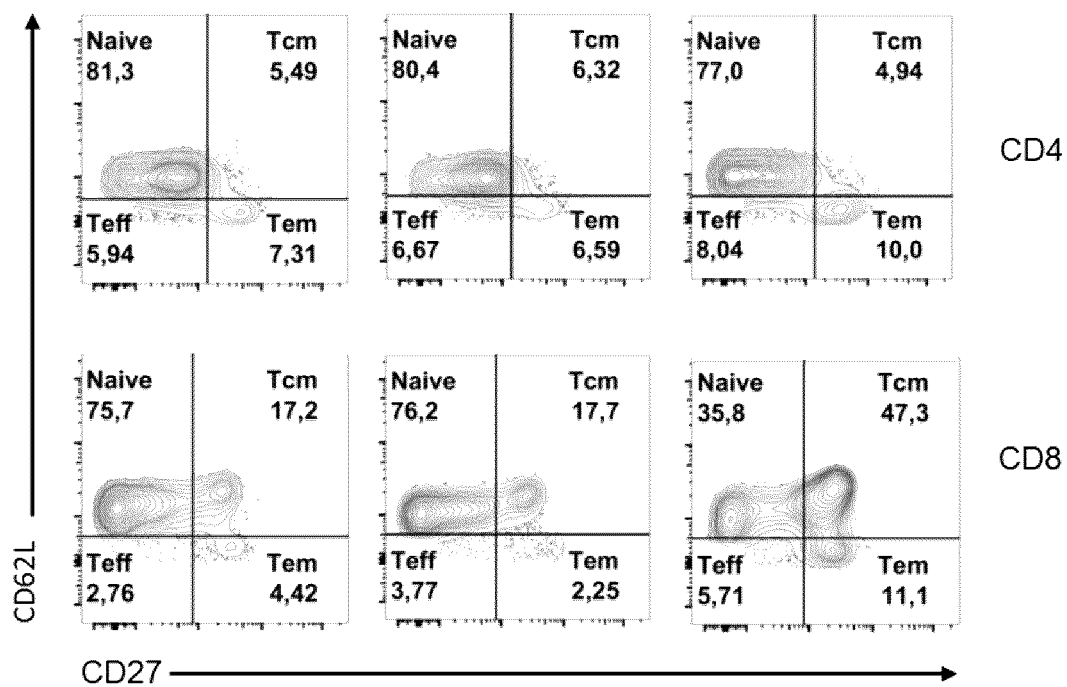
FIG. 5B illustrates CD4 and CD8 T cell populations in lymph nodes of ptpn1$^{fl/fl}$/ptpn2$^{fl/fl}$;E8iCre mice. Flow cytometric analysis of lymph node cell suspensions stained with antibodies for CD4, CD8, CD62L and CD44. Shown are CD62L vs CD44 plots of cells gated on CD4+ and CD8+ single positive T lymphocytes from 5A. The quadrants delineate naive, central memory (Tcm), effector memory (Tem) and effector (Teff) cells to demonstrate the spontaneous increase of Tcm populations in DKO mice.

Together the results of FIGS. 5A and 5B illustrate how genetic deficiency of PTPN1 and PTPN2, either partial (double heterozygous; DHet) of absolute (double knockout; DKO), does not affect the development of CD8 single positive T cells. These cells are found in immune peripheral organs as lymph nodes (LNs) of DHet and DKO mice. Strickingly, despite a decrease in the proportion of cells regarding total LN mononuclear cells an increase of almost 3 times was observed in cells differentiated into the Tcm compartment. An increase in the effector/memory (Teff and Tem) compartments was also observed indicating an increases sensitivity to activation of CD8 T cells from the DKO mouse with a differentiation biased toward the Tcm phenotype. This series of experiments is the first demonstration that concomitant inhibition of the activities of PTPN1 and PTPN2 (PTP-1B and TC-PTP) has a major effect in the enhancement of the memory qualities of CD8 T cells. Tcm is a memory phenotype that is desirable in T cell immunotherapies [Berger et al., J Clin Invest. 2008118(1): 294-305].

Figure 6A:
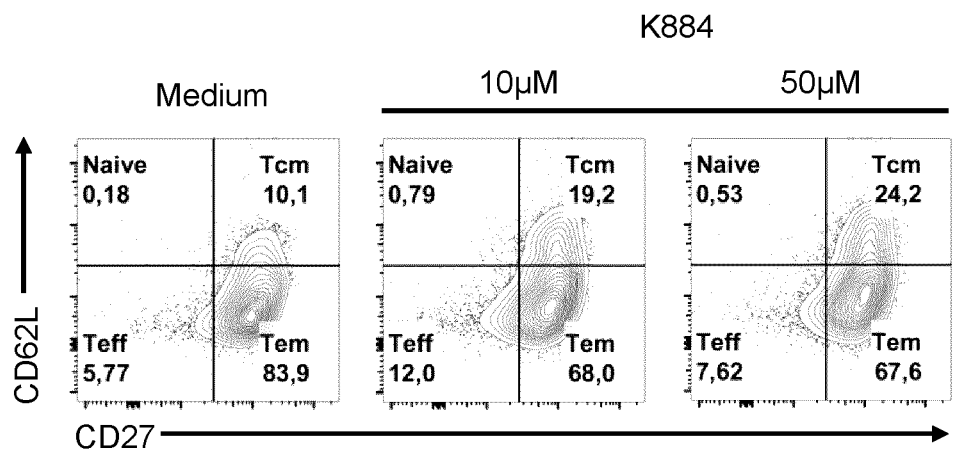
FIG. 6A illustrates the pharmacological inhibition of PTPN1/2 that enhances Tcm differentiation of CD8 T cells and increases their expression of activation markers. Flow cytometric analysis of in vitro differentiated CTLs from CD57BL/6 mice in presence or absence of the PTPN1/2 inhibitor K884. Shown are plots of cells gated live CD8+ cells and stained for CD62L and CD27 with specific antibodies.
Figure 6B:
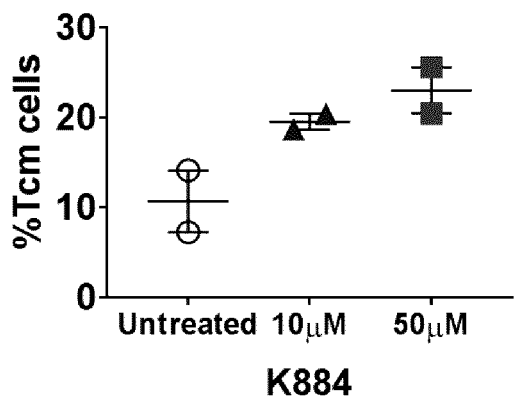
FIG. 6B illustrates the pharmacological inhibition of PTPN1/2 that enhances Tcm differentiation of CD8 T cells and increases their expression of activation markers. Flow cytometric analysis of in vitro differentiated CTLs from CD57BL/6 mice in presence or absence of the PTPN1/2 inhibitor K884. Shown are frequencies of Tcm cells (CD62L$^{high}$-CD27$^{high}$) cells expressed as percentage of gated cells in the different conditions tested. Each data point represents the mean of duplicate readings from individual mice (n=2).
Figure 6C:
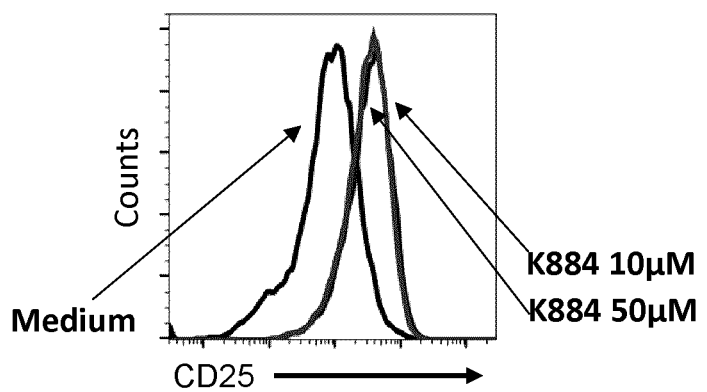
FIG. 6C illustrates the pharmacological inhibition of PTPN1/2 that enhances Tcm differentiation of CD8 T cells and increases their expression of activation markers. Flow cytometric analysis of in vitro differentiated CTLs from CD57BL/6 mice in presence or absence of the PTPN1/2 inhibitor K884. Shown are frequencies of Tcm cells (CD62L$^{high}$-CD27$^{high}$) cells expressed as percentage of gated cells in the different conditions tested. Show is CD25 expression in cells from the Tcm gate under the different conditions tested.

FIGS. 6A, 6B and 6C shows that pharmacological inhibition of PTPN1 and PTPN2 with the compound K884 in mouse activated CD8 T induced an increased differentiation into Tcm cells at higher rates than the observed in untreated cells. When the activated CD8 cells were stained to assess the expression of the IL-2 receptor alpha (CD25), upregulated after activation and broadly used as functional marker, CD8 cells treated with K884 showed an increase on fluorescence closer to one order of magnitude when compared to the untreated ones. These data demonstrated that the PTPN1/2 inhibitor K884 reproduces the phenotype displayed by the genetic double deficient model, confirming the specificity of the K884 compound on inhibiting the phosphatases PTPN1 and PTPN2, and showing its capacity to enhance activation of CD8 cells and increase the proportion of cells differentiated into Tcm cells.

Figure 7A:
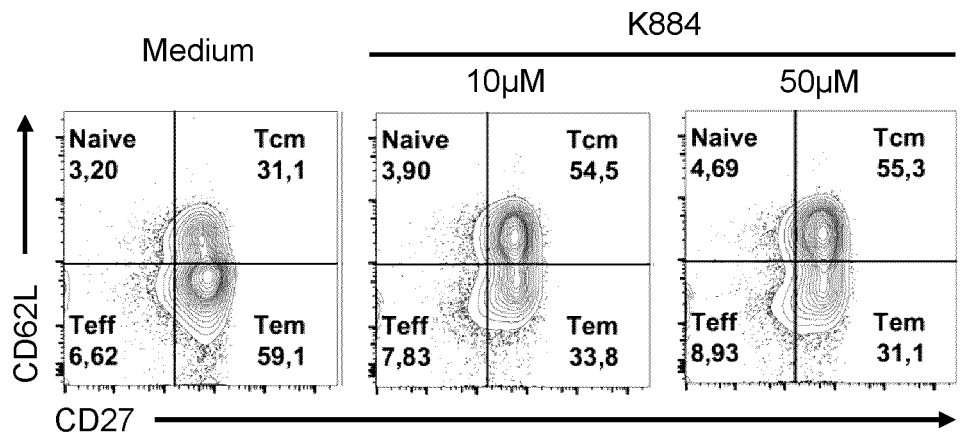
FIG. 7A illustrates that the inhibition of PTPN1/2 has an additive effect in the IL-15 induction of memory T cells. Flow cytometric analysis of C57BL/6 CTLs differentiated in presence or absence of K884 furtherly incubated with murine IL-15 for 5 days, maintaining the respective K884 concentration. Shown are cells that were stained and gated as in FIG. 2A.
Figure 7B:
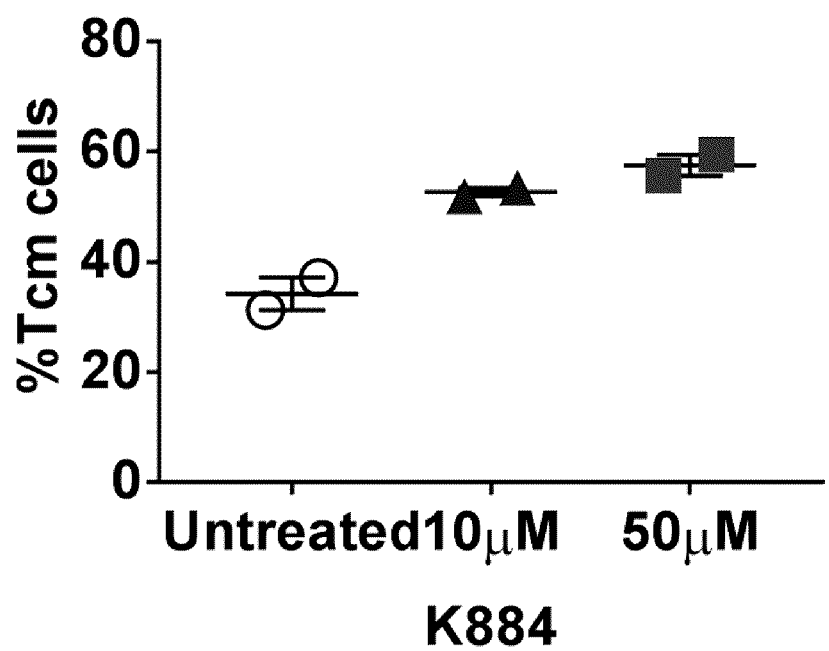
FIG. 7B illustrates that the inhibition of PTPN1/2 has an additive effect in the IL-15 induction of memory T cells. Flow cytometric analysis of C57BL/6 CTLs differentiated in presence or absence of K884 furtherly incubated with murine IL-15 for 5 days, maintaining the respective K884 concentration. Shown are the percentage of Tcm cells for the different conditions (n=2). Each data point represents the mean of duplicate readings from individual mice.

IL-15 is a potent homeostatic cytokine known to favor the differentiation of activated CD8 T cells into memory cells, including Tcm. FIGS. 7A and 7B show activated CD8 T cells as in FIG. 6, followed by 5 days incubated with recombinant murine IL-15 in presence of the PTPN1/2 inhibitor K884. In both, untreated controls and K884 treated cells, an increase on the fraction of Tcm cells was evident when compared with the respective baseline (FIG. 6A). Although the proportion of cells does not show linearity in K884 treated cells when compared to untreated cells, the percentage of Tcm population in K884 treated incubated with IL-15 cells was still almost 2 times larger than the observed in cells with IL-15 alone. Hence, the ability of K884 to increase the percentage of Tcm cells is maintained after IL-15 incorporation on the CD8 cells media. Then, the inhibition of PTPN1/2 had an additive effect to IL-15 on the differentiation of CD8 T cells into Tcm.

Figure 8:
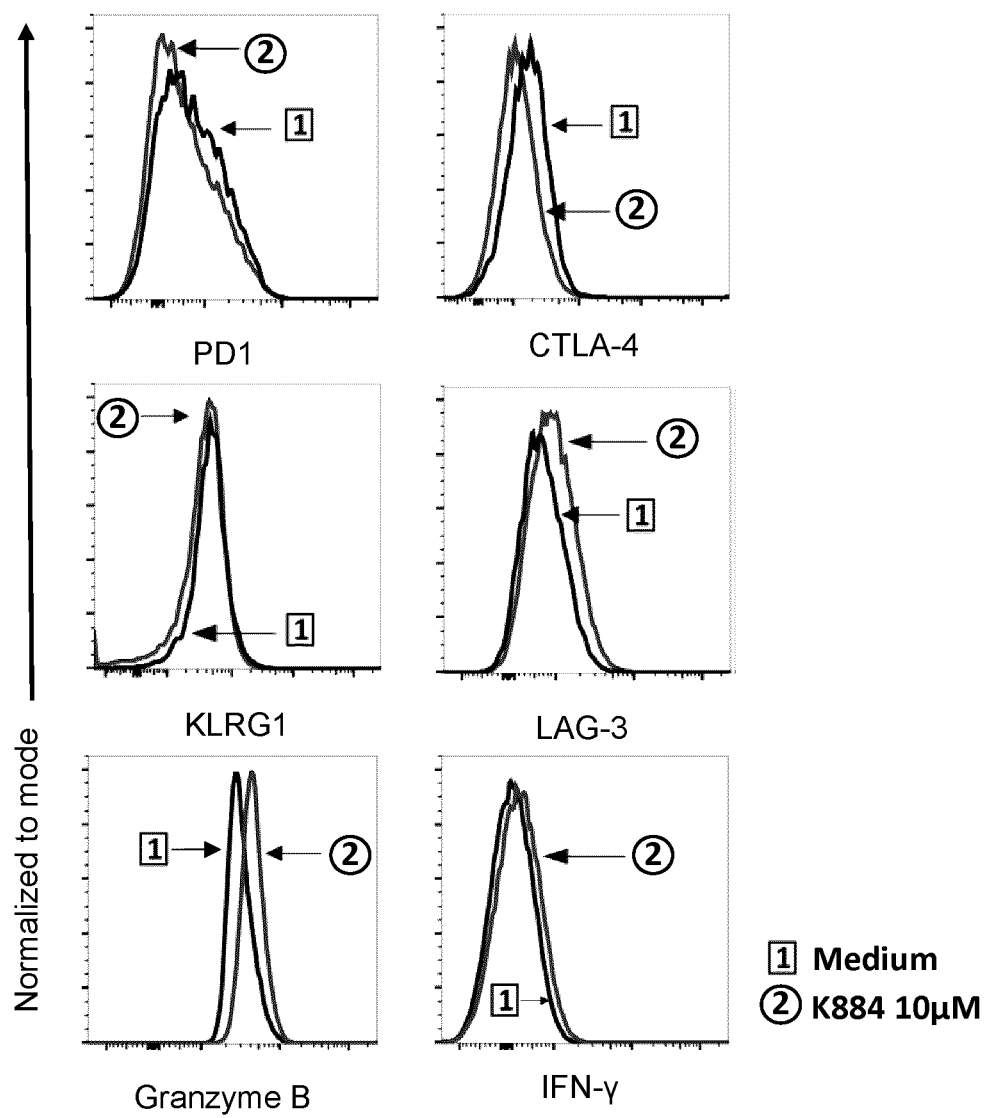
FIG. 8 illustrates that pharmacological inhibition of PTPN1/2 reduces expression of exhaustion markers and increases effector-molecule expression after CTL re-stimulation. Flow cytometric analysis of CD8 T cells differentiated into Tcm cells after 5 days of a second stimulation with anti-CD3 and anti-CD28 in presence or absence of K884. Histograms show the expression of exhaustion markers PD-1, CTLA-4, KLRG1 and LAG-3, and granzyme B and IFN-γ as markers of effector CTLs. Cells are gated on live/CD8+/CD62L$^{high}$.

In FIG. 8 cells activated as in FIG. 6 are stimulated once again with anti-CD3, anti-CD28 and IL-2 for 5 days and expression of receptors associated with T cell exhaustion was assessed by flow cytometry. K884 treated cells displayed less exhaustion markers PD-1, CDTLA4 and KLRG1. Opposite to other exhaustion markers, an increased expression of the receptor LAG-3, was observed, however when expressed alone LAG-3 is characteristic of cells expressing high levels of the proinflammatory cytokine IFN-gamma [Demeure, C E, et al, 37(13), 2001, p. 1709-1718]. These cells also displayed higher levels of Granzyme B and IFN-gamma. Together these results show that treatment with K884 enhances functional markers of cytotoxicity while inducing resistance to the expression of exhaustion markers after restimulation.

Figure 9A:
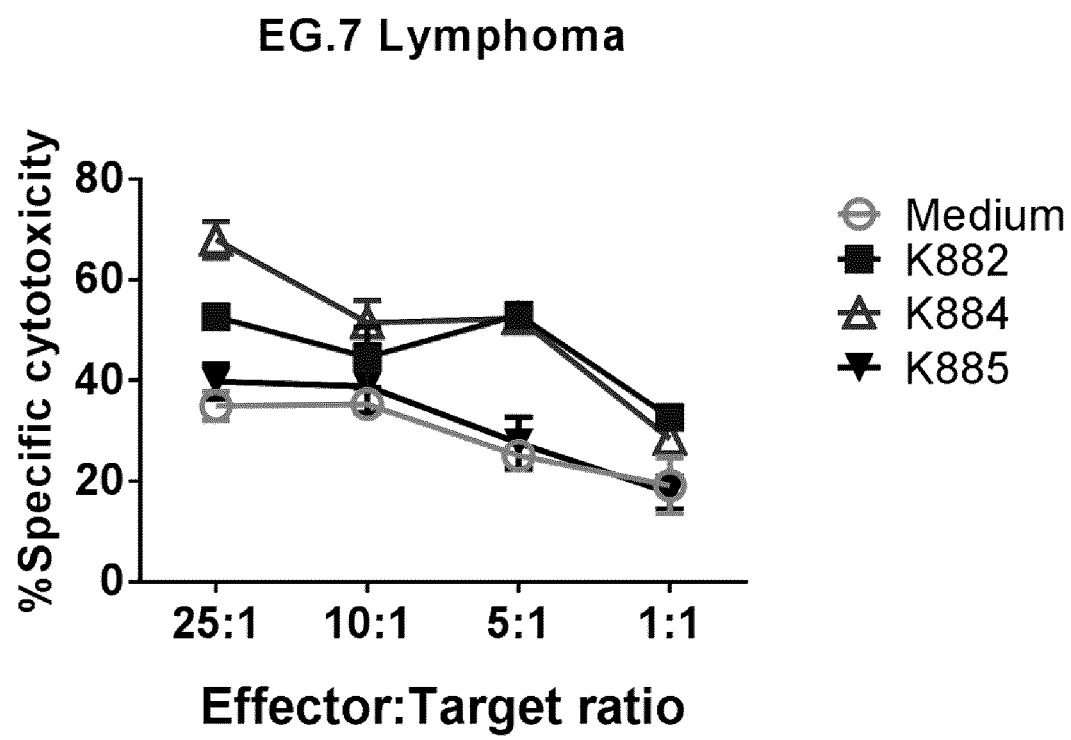
FIG. 9A illustrates that the pharmacological inhibition of PTPN1/2 enhances the cytotoxic activity of CTLs. Calcein-release cytotoxic assays of OT-1 transgenic CD8 T cells after 5-day differentiation into CTLs in presence or absence of the PTPN1/2 inhibitors K882, K884 and K885 at 50 µM. Show is an experiment where effector OT-1 CTL cells were incubated with Calcein-loaded OVA expressing EG.7 lymphoma target cells for 5 hours at different effector to target ratios. Experiments were plated in duplicate, mean and range are shown.
Figure 9B:
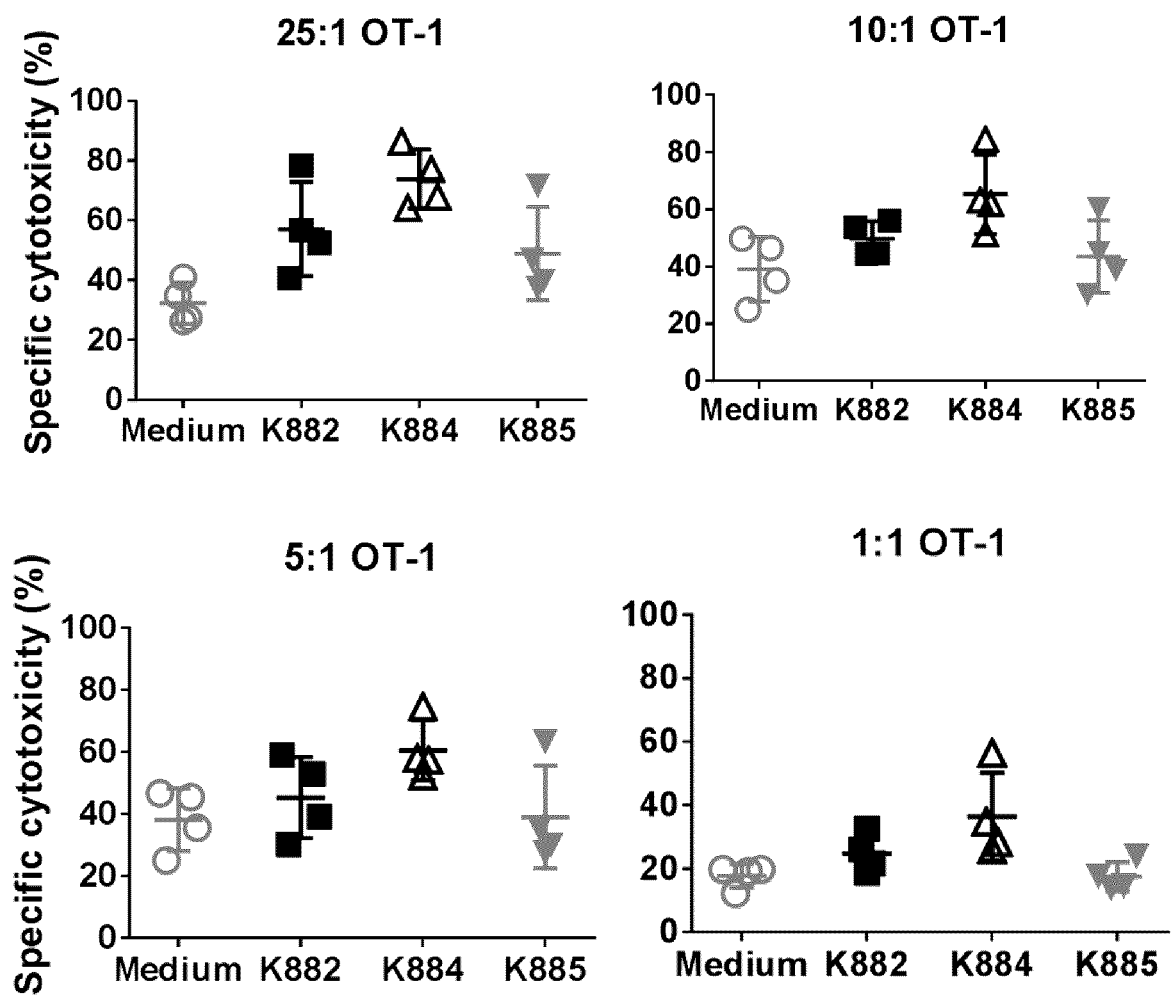
FIG. 9B illustrates that the pharmacological inhibition of PTPN1/2 enhances the cytotoxic activity of CTLs. Calcein-release cytotoxic assays of OT-1 transgenic CD8 T cells after 5-day differentiation into CTLs in presence or absence of the PTPN1/2 inhibitors K882, K884 and K885 at 50 µM. Shown are means and standard deviation of CTLs from a group of 4 animals tested as in A.

FIGS. 9A and 9B show the ability of activated CD8 T cells to lyse target lymphoma cells expressing the specific antigen in presence or absence of the PTPN1/2 inhibitors K882, K884 and K885. To this mean, CD8 OT-1 cells (specific for an epitope of chicken egg ovalbumin [OVA]) were purified and stimulated as in FIG. 6. Cells were then incubated for 5 hours at different ratios with an EL-4 lymphoma derivative cell line expressing OVA, EG-7. At every effector to target ratio OT-1 cells activated in presence of K884 lysed EG.7 cells with greater efficiency (specific cytotoxicity) than untreated cells or cells activated in presence of the PTPN1/2 inhibitors K882 or K885. These results demonstrate how the pharmacological inhibition of both PTPN1 and PTPN2 enhance the ability of CD8 T cells to eliminate tumoral cell expressing the specific antigen and that K884 was the most potent of the PTPN1/2 inhibitors tested.

Figure 10A:
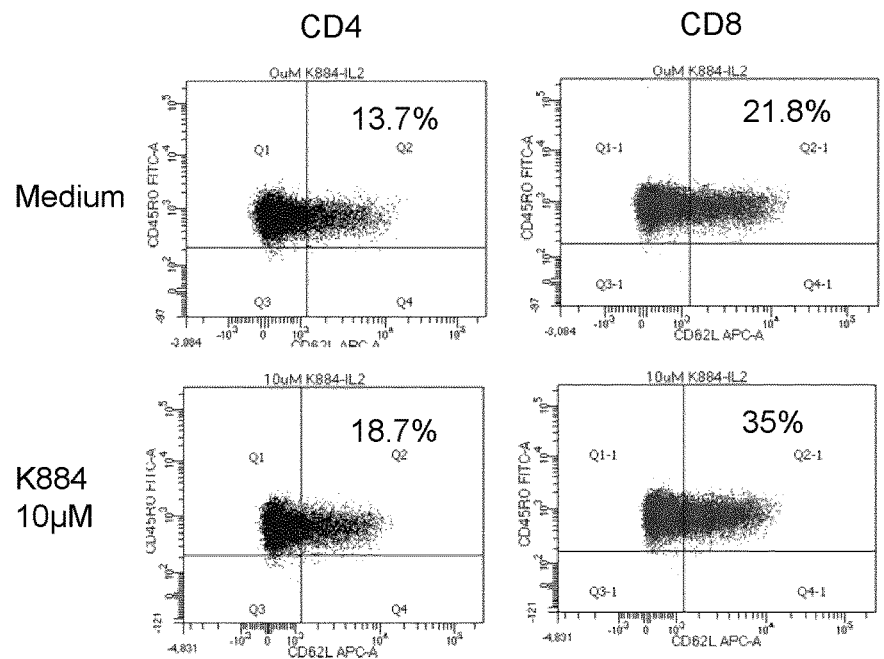
FIG. 10A illustrates the effects of K884 in human T cells central memory differentiation in vitro. Plots show T cells from human donors after stimulation with anti-CD3, anti-CD28 and IL-2 in presence or absence of the indicated concentration of the PTPN1/2 inhibitor K884 for 7 days. Cells were stained with CD4, CD8, CD62L and CD45RO specific antibodies to identify human Tcm cells (CD45RO+, CD62L$^{high}$).
Figure 10B:
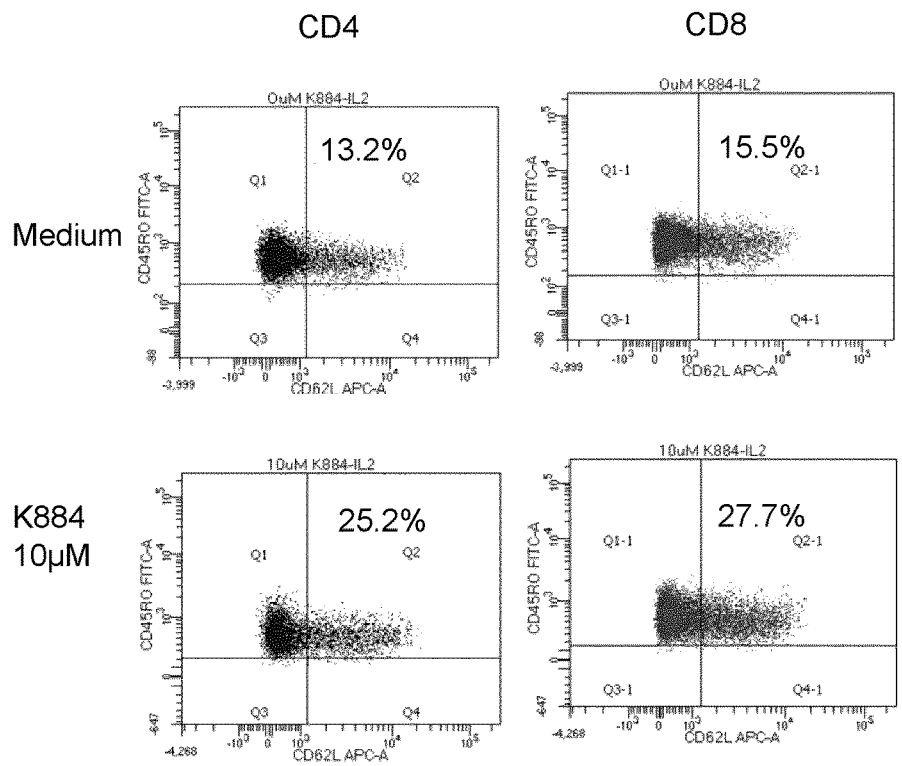
FIG. 10B illustrates the effects of K884 in human T cells central memory differentiation in vitro. Plots show T cells from human donors after stimulation with anti-CD3, anti-CD28 and IL-2 in presence or absence of the indicated concentration of the PTPN1/2 inhibitor K884 for 14 days. Cells were stained with CD4, CD8, CD62L and CD45RO specific antibodies to identify human Tcm cells (CD45RO+, CD62L$^{high}$).
Figure 10C:
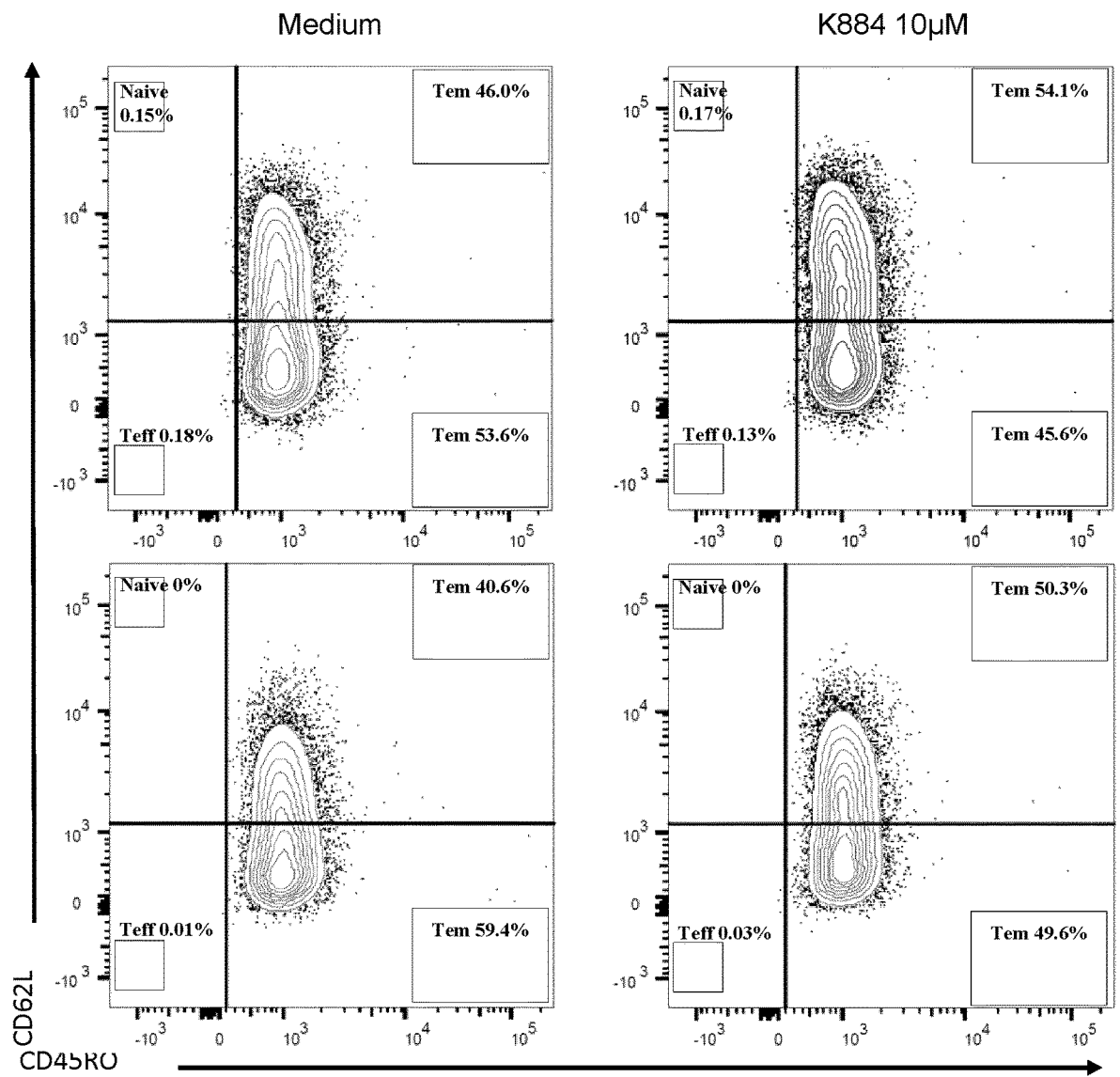
FIG. 10C illustrates the effects of K884 in human T cells central memory differentiation in vitro. Plots show T cells from human donors after stimulation with anti-CD3, anti-CD28, and cytokines IL-7 and IL-15 in presence or absence of the indicated concentration of the PTPN1/2 inhibitor K884 for 14 days. Cells were stained with CD4, CD8, CD62L and CD45RO specific antibodies to identify human Tcm cells (CD45RO+, CD62L$^{high}$).
Figure 10D:
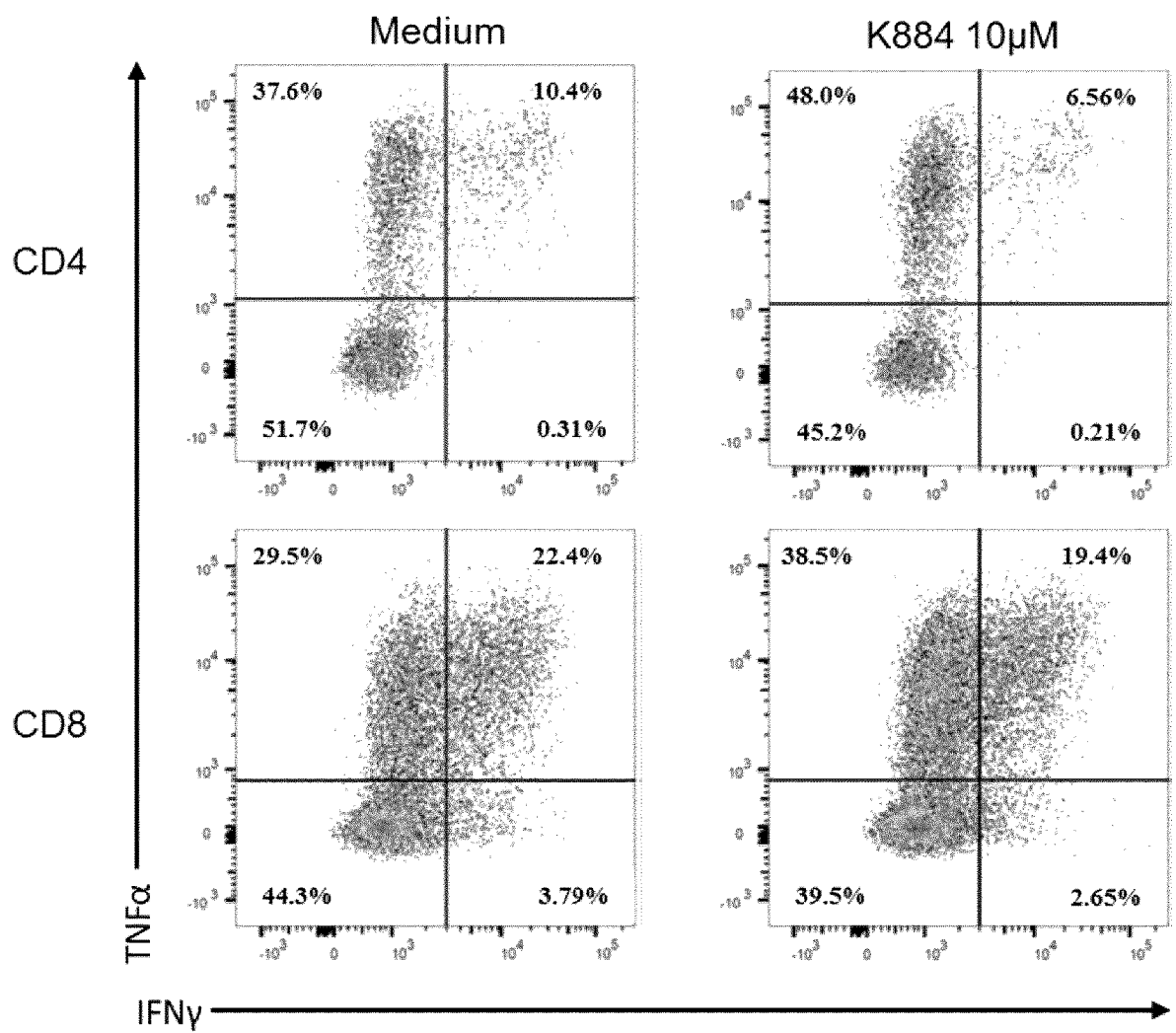
FIG. 10D illustrates that the pharmacological inhibition of PTPN1/2 enhances cytokine production in CD4 and CD8 human T cells in culture. Flow cytometric analysis of human T cells stimulated with anti-CD3/CD28 and cultured during 14 days with IL-7 and IL-15 in presence or absence of the PTPN1/2 inhibitor K884. To determine cytokine production, cells were restimulated with PMA and Ionomycin during 4 hours before staining with appropriate antibodies.

FIGS. 10A to 10D present results assessing the differentiation into Tcm cells obtained from human cells stimulated in similar conditions to those tested in FIGS. 6 and 7 on mouse cells. The results also show that in human CD4 cells a similar enhancement of the Tcm populations are observed (FIGS. 10 A to 10C). FIG. 10D shows that there is also an enhancement of the proinflammatory cytokine TNFα secretion while production of IFNγ is maintained. All together, data in FIG. 10 demonstrates that peripheral blood human CD8 T cells respond in equivalent manner to mouse CD8 T cells to treatment with the PTPN1/2 inhibitor K884.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. An ex vivo method of stimulating an isolated memory T-cell, tumor-infiltrating lymphocyte (TIL), T cell receptor (TCR) engineered cell, and/or chimeric antigen receptor (CAR) engineered cell comprising:
treating an isolated memory T-cell, tumor-infiltrating lymphocyte (TIL), T cell receptor (TCR) engineered cell, and/or chimeric antigen receptor (CAR) engineered cell with an effective amount of a compound of structural Formula I, or a pharmaceutically acceptable salts thereof, and stereoisomers thereof:

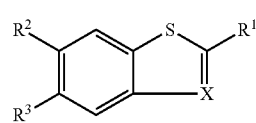

wherein:
X is selected from CH and N;
$R^1$ is selected from the group consisting of (a) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (b) —(C=O)$R^4$; (c) —CN; (d) —(C=O)O$R^4$; (e) —(C=O)NH$R^4$; (f) —(C=O)N$R^5R^6$; and (g) aryl or heteroaryl wherein the aryl and heteroaryl group itself may be optionally substituted with 1-3 substituents independently selected from (i) halogen, (ii) —(C=O)O$C_{1-3}$ alkyl optionally substituted with 1-3 halogens, (iii) —COOH (iv) $C_{1-3}$ alkyl optionally substituted with 1-3 halogens, (v) —$OC_{1-3}$ alkyl optionally substituted with 1-3 halogens, (vi) —$SO_x$Me, (vii) —CN, and (viii) —$SO_2NH_2$;
$R^2$ and $R^3$ are independently selected from the group consisting of (a) halogen; (b) difluoromethylphosphonic acid;
$R^4$ is selected from the group consisting of (a) H; (b) $C_{1-3}$ alkyl optionally substituted with 1-5 halogens and optionally with one group selected from —OH, —$OC_{1-3}$ alkyl optionally substituted with 1-3 halogens, —$SO_xC_{1-3}$ alkyl, and —CN; (d) aryl or heteroaryl wherein the aryl or heteroaryl group itself may be optionally substituted by 1-3 halogens, $C_{1-3}$ alkyl or $C_{1-3}$haloalkyl;

R$^5$ and R$^6$ are independently selected from the group consisting of (a) C$_{1-3}$ alkyl optionally substituted with 1-5 halogens and optionally with one group selected from —OH, —OC$_{1-3}$ alkyl optionally substituted with 1-3 halogens, —SO$_x$C$_{1-3}$ alkyl, and —CN; (b) aryl or heteroaryl wherein the aryl or heteroaryl group itself may be optionally substituted by 1-3 halogens, C$_{1-3}$ alkyl or C$_{1-3}$ haloalkyl;

R$^5$ and R$^6$, together with the nitrogen atom to which they are attached may be joined to form a 5- to 7-membered ring, which may be substituted with 1-3 groups independently selected from (i) halogen, (ii) —(C=O)OC$_{1-3}$ alkyl, (iii) —(C=O)OH (iv) C$_{1-3}$ alkyl optionally substituted with 1-3 halogens, (v) —OC$_{1-3}$ alkyl optionally substituted with 1-3 halogens, (vi) —OH, (vii) C$_{1-3}$ hydroxyalkyl, (viii) aryl or heteroaryl wherein the aryl or heteroaryl group itself may be optionally substituted by 1-3 halogens, C$_{1-3}$ alkyl or C$_{1-3}$ haloalkyl; and x is an integer from 0 to 2.

2. The ex vivo method of claim 1, wherein said compound is of structural Formula Ia, or a pharmaceutically acceptable salts thereof, and stereoisomers thereof:

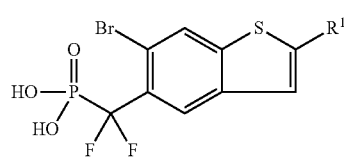

Ia wherein:
R$^1$ is selected from the group consisting of (a) C$_{1-3}$ alkyl optionally substituted with 1-5 halogens and optionally with one group selected from —OH, —OC$_{1-3}$ alkyl optionally substituted with 1-3 halogens, and —CN; (b) —(C=O)R$^4$; (c) —CN; (d) —(C=O)OR$^4$; (e) —(C=O)NHR$^4$; and (f) —(C=O)NR$^5$R$^6$;

R$^4$ is selected from the group consisting of (a) H; and (b) C$_{1-3}$ alkyl optionally substituted with 1-5 halogens;

R$^5$ and R$^6$ are independently selected from the group consisting of C$_{1-3}$ alkyl optionally substituted with 1-5 halogens and optionally with one group selected from —OH, and —OC$_{1-3}$ alkyl optionally substituted with 1-3 halogens; and R$^5$ and R$^6$, together with the nitrogen atom to which they are attached may be joined to form a 5- to 7-membered ring, which may be substituted with a 1-3 groups independently selected from (i) halogen, (ii) C$_{1-3}$ alkyl optionally substituted with 1-3 halogens, (iii) —OC$_{1-3}$ alkyl optionally substituted with 1-3 halogens, (iv) —OH, and (vii) C$_{1-3}$ hydroxyalkyl.

3. The ex vivo method of claim 1, wherein said compound is of structural Formula Ib, or a pharmaceutically acceptable salts thereof, and stereoisomers thereof:

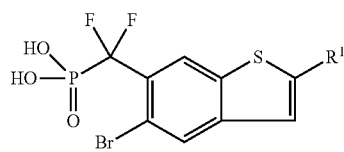

Ib wherein:
R$^1$ is selected from the group consisting of (a) C$_{1-3}$ alkyl optionally substituted with 1-5 halogens and optionally with one group selected from —OH, —OC$_{1-3}$ alkyl optionally substituted with 1-3 halogens, and —CN; (b) —(C=O)R$^4$; (c) —CN; (d) —(C=O)OR$^4$; (e) —(C=O)NHR$^4$; and (f) —(C=O)NR$^5$R$^6$;

R$^4$ is selected from the group consisting of (a) H; and (b) C$_{1-3}$ alkyl optionally substituted with 1-5 halogens;

R$^5$ and R$^6$ are independently selected from the group consisting of C$_{1-3}$ alkyl optionally substituted with 1-5 halogens and optionally with one group selected from —OH, and —OC$_{1-3}$ alkyl optionally substituted with 1-3 halogens; and R$^5$ and R$^6$, together with the nitrogen atom to which they are attached may be joined to form a 5- to 7-membered ring, which may be substituted with a 1-3 groups independently selected from (i) halogen, (ii) C$_{1-3}$ alkyl optionally substituted with 1-3 halogens, (iii) —OC$_{1-3}$ alkyl optionally substituted with 1-3 halogens, (iv) —OH, and (vii) C$_{1-3}$ hydroxyalkyl.

4. The ex vivo method of claim 1, wherein said compound is a compound selected from the following compounds:

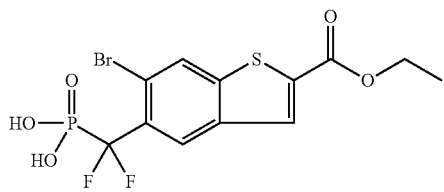 [SMILES: CCOC(=O)c1cc2cc(C(F)(F)P(=O)(O)O)c(Br)cc2s1]

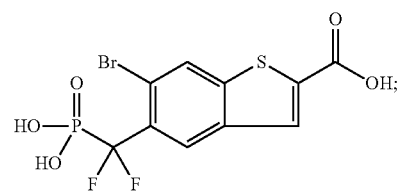

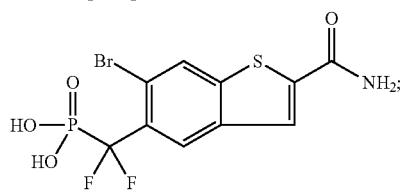

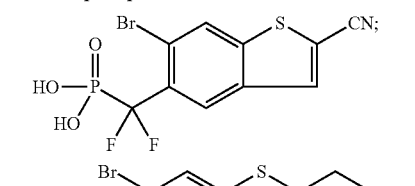

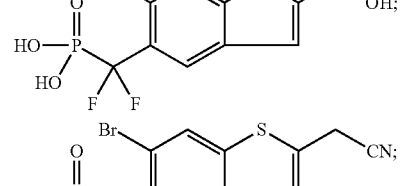

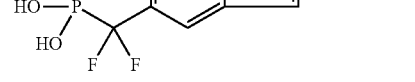

-continued

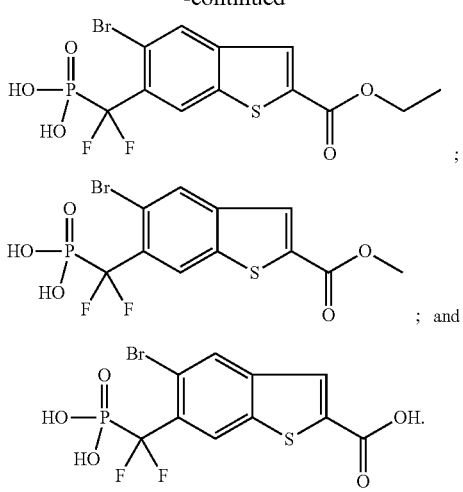

5. The ex vivo method of claim 2, wherein said compound is selected from the following compounds:

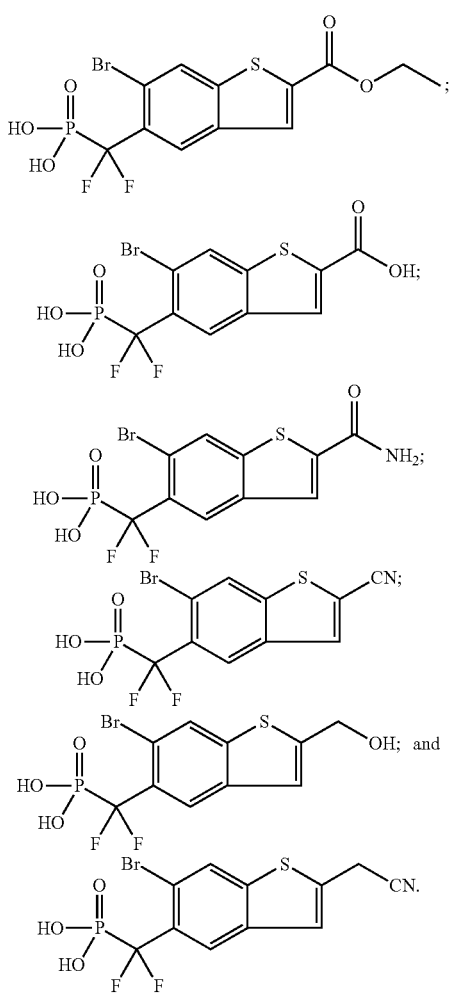

6. The ex vivo method of claim 3, wherein said compound of is selected from the following compounds:

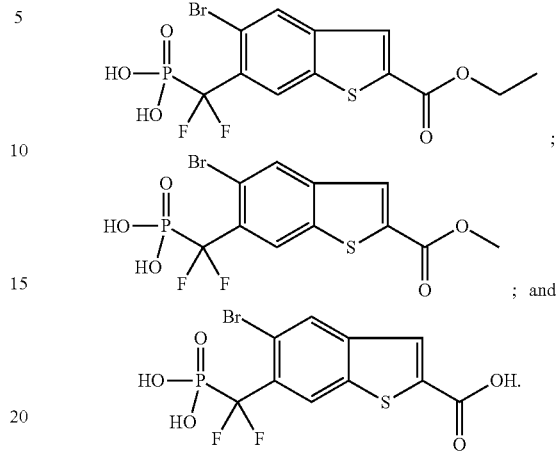

7. The ex vivo method claim 2, wherein said compound is

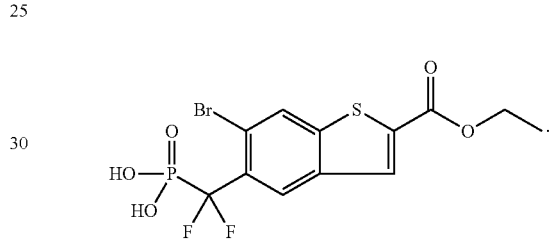

8. The ex vivo method of claim 1, wherein treating is under activating conditions and/or further comprising the step of activating said isolated memory T-cell, tumor-infiltrating lymphocyte (TIL), T cell receptor (TCR) engineered cell, and/or chimeric antigen receptor (CAR) engineered cell before, during or after treatment with said compound of formula I, Ia or Ib.

9. The ex vivo method of claim 8, wherein said activating conditions or said step of activating comprises treatment with a cytokine, a chemokine, a growth factor, a T-cell associated check-point inhibitor, a tumor associated check-point inhibitor, antibodies recognizing CD3 and CD28 receptors, autologous or allogeneic dendritic cells loaded with the specific antigen, any other antigen presenting cell (APC) loaded with the specific antigen, irradiated tumor cells treated or not with proinflammatory cytokines as type 1 and type 2 interferons, and combinations thereof.

10. The ex vivo method of claim 1, wherein treating is for a time sufficient for expansion, transduction or activation of said isolated memory T-cell, tumor-infiltrating lymphocyte (TIL), T cell receptor (TCR) engineered cell, and/or chimeric antigen receptor (CAR) engineered cell.

11. The ex vivo method of claim 1, wherein said isolated tumor-infiltrating lymphocyte is harvested from a patient.

12. The ex vivo method of claim 8, further comprising the step of isolating memory T-cell, tumor-infiltrating lymphocyte (TIL), activated T cell receptor (TCR) engineered cell, and/or activated chimeric antigen receptor (CAR) engineered cell.

* * * * *